United States Patent
Nowick et al.

(10) Patent No.: US 11,046,730 B2
(45) Date of Patent: Jun. 29, 2021

(54) ANTIMICROBIAL COMPOSITIONS

(71) Applicant: The Regents of the University of California, Oakland, CA (US)

(72) Inventors: James S. Nowick, Irvine, CA (US); Hyun Jun Yang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/091,907

(22) PCT Filed: Apr. 17, 2017

(86) PCT No.: PCT/US2017/027923
§ 371 (c)(1),
(2) Date: Oct. 5, 2018

(87) PCT Pub. No.: WO2017/181179
PCT Pub. Date: Oct. 19, 2017

(65) Prior Publication Data
US 2019/0112335 A1    Apr. 18, 2019

Related U.S. Application Data

(60) Provisional application No. 62/322,911, filed on Apr. 15, 2016.

(51) Int. Cl.
*A61K 38/12* (2006.01)
*A61K 38/15* (2006.01)
(Continued)

(52) U.S. Cl.
CPC ............... *C07K 7/06* (2013.01); *A61K 38/12* (2013.01); *A61K 38/15* (2013.01); *A61P 31/04* (2018.01);
(Continued)

(58) Field of Classification Search
CPC ........ A61K 38/08; A61K 38/12; A61K 38/15; C07K 7/06; C07K 7/50–56; C07K 7/64; C07K 11/02
See application file for complete search history.

(56) References Cited

U.S. PATENT DOCUMENTS 9,163,065 B2    10/2015   Peoples et al.
2010/0056435 A1   3/2010   Ganesan et al.
(Continued)

FOREIGN PATENT DOCUMENTS

EP    3443078 A1    2/2019
WO    2014089053 A1    6/2014
(Continued)

OTHER PUBLICATIONS

International Preliminary Report on Patentability for International Application PCT/US2017/027923, Report dated Oct. 16, 2018, dated Oct. 25, 2018, 6 Pgs.
(Continued)

*Primary Examiner* — Jeffrey E. Russel
(74) *Attorney, Agent, or Firm* — KPPB LLP

(57) ABSTRACT

Antimicrobial molecules, their synthesis and use as antimicrobial treatments are described. The antimicrobial compounds are teixobactin analogues. Methods of synthesizing antimicrobial teixobactin analogues are also provided. Antibiotic therapeutics comprising antimicrobial teixobactin analogues are provided, along with methods of and formulations for treating microbial infections using such antimicrobial teixobactin analogues. Prodrugs formed using esterified forms of antimicrobial teixobactin analogues may also be provided.

17 Claims, 16 Drawing Sheets

(51) Int. Cl.
*C07K 7/56* (2006.01)
*C07K 11/02* (2006.01)
*C07K 7/06* (2006.01)
*A61P 31/04* (2006.01)
*A61K 38/00* (2006.01)

(52) U.S. Cl.
CPC ............... *C07K 7/56* (2013.01); *C07K 11/02* (2013.01); *A61K 38/00* (2013.01)

(56) References Cited

U.S. PATENT DOCUMENTS

| | | | |
|---|---|---|---|
| 2011/0269698 | A1 | 11/2011 | Lee et al. |
| 2015/0259386 | A1 | 9/2015 | Fliri et al. |
| 2020/0216493 | A1* | 7/2020 | Henninot ................ C07K 7/06 |

FOREIGN PATENT DOCUMENTS

| | | |
|---|---|---|
| WO | 2015031871 A1 | 3/2015 |
| WO | 2017181179 A1 | 10/2017 |

OTHER PUBLICATIONS

International Search Report and Written Opinion for International Application No. PCT/US2017/027923, Search completed Jun. 15, 2017, dated Jul. 19, 2017, 12 Pgs.
"Antibiotic Resistance Threats in the United States, 2013", U.S. Department of Health and Human Services, Centers for Disease Control and Prevention, Nov. 30, 2013, 114 pgs.
"Reasons to be cheerful", Nature, Jan. 8, 2015, vol. 517, 121, doi: 10.1038/517121a.
Abdel Monaim et al., "Lysine Scanning of Arg10-Teixobactin: Deciphering the Role of Hydrophobic and Hydrophilic Residues", ACS Omega, Dec. 19, 2016, vol. 1, pp. 1262-1265, doi: 10.1021/acsomega.6b00354.
Abdel Monaim et al., "Re-evaluation of the N-terminal substitution and the D-residues of teixobactin", RSC Advances, 2016, vol. 6, pp. 73827-73829, doi: 10.1039/C6RA17720D.
Agha et al., "Oligopeptides as Biomarkers of Cyanobacterial Subpopulations. Toward an Understanding of Their Biological Role", Toxins, Jun. 23, 2014 (Jun. 23, 2014), vol. 6, p. 1929-1950; Abstract, p. 1932.
Breukink et al., "Lipid II as a target for antibiotics", Nature Reviews, Drug Discovery, Mar. 10, 2006, vol. 5, pp. 321-332, doi: 10.1038/nrd2004.
Cockerill, III et al., "Methods for Dilution Antimicrobial Susceptibility Tests for Bacteria That Grow Aerobically. Approved Standard", Clinical and Laboratory Standards Institute—Ninth Edition, Jan. 2012, CLSI document M07-A9, vol. 32, No. 2, 88 pgs.
Craig et al., "A Highly Stereoselective and Scalable Synthesis of I-allo-Enduracididine", Organic Letters, Sep. 10, 2015, vol. 17, pp. 4620-4623, doi: 10.1021/acs.orglett.5b02362.
Davies, "The cyclization of peptides and depsipeptides", Journal of Peptide Science, Aug. 2003, vol. 9, pp. 471-501, doi: 10.1002/psc.491.
De Kruijff et al., "Lipid II: a central component in bacterial cell wall synthesis and a target for antibiotics", Prostaglandins Leukot Essent Fatty Acids, Sep.-Nov. 2008, vol. 79, No. 3-5, pp. 117-121, doi: 10.1016/j.plefa.2008.09.020.
Dhara et al., "Solution-Phase Synthesis of the Macrocyclic Core of Teixobactin", European Journal of Organic Chemistry, Jul. 29, 2016, vol. 2016, pp. 4289-4293, doi: 10.1002/ejoc.201600778.
Furumai et al., "FK228 (Depsipeptide) as a Natural Prodrug That Inhibits Class I Histone Deacetylases", Cancer Research, Sep. 1, 2002 (Sep. 1, 2002), vol. 62, p. 4916-4921;Title, p. 4917.
Giltrap et al., "Total Synthesis of Teixobactin", Organic Letters, May 18, 2016, vol. 18, No. 11, pp. 2788-2791, doi: 10.1021/acs.orglett.6b01324.

Grady, "New Antibiotic Stirs Hope Against Resistant Bacteria", The New York Times, Jan. 7, 2015, Retrieved from the Internet http://www.nytimes.com/2015/01/08/health/from-a-pile-of-dirt-hope-for-a-powerful-new-antibiotic.html, 4 pgs.
Hsu et al., "The nisin-lipid II complex reveals a pyrophosphate cage that provides a blueprint for novel antibiotics", Nat. Struct. Mol. Biol., 2004, vol. 11, pp. 963-967, doi: 10.1038/nsmb830.
Jad et al., "Synthesis and Biological Evaluation of a Teixobactin Analogue", Organic Letters, Dec. 10, 2015, vol. 17, pp. 6182-6185, doi: 10.1021/acs.orglett.5b03176.
Jin et al., "Total synthesis of teixobactin", Nature Communications, Aug. 3, 2016, vol. 7, No. 12394, pp. 1-6, doi: 10.1038/ncomms12394.
Kahrstrom, "Antibacterial drugs: a new drug for resistant bugs", Nature Reviews, Drug Discovery, Feb. 2015, vol. 14, No. 2, pp. 94, doi: 10.1038/nrd4544.
Kahrstrom, "Antimicrobials: a new drug for resistant bugs", Nature Reviews Microbiology, Mar. 2015, vol. 13, 1 pg., doi:10.1038/nrmicro3429.
Kling et al., "Antibiotics. Targeting DnaN for tuberculosis therapy using novel griselimycins", Science, Jun. 5, 2015, vol. 348, Issue 6239, pp. 1106-1112, doi: 10.1126/science.aaa4690.
Lambert et al., "The synthesis of cyclic peptides", Journal of the Chemical Society, Perkin Transactions 1, Feb. 14, 2001, pp. 471-484, doi: 10.1039/B001942I.
Ledford, "Promising antibiotic discovered in microbial 'dark matter, Nature'", Jan. 7, 2015, pgs., doi: 10.1038/nature.2015.16675.
Ling et al., "A new antibiotic kills pathogens without detectable resistance", Nature, Jan. 22, 2015, vol. 517, pp. 455-459, doi: 10.1038/nature14098.
Möschwitzer et al., "Asymmetric synthesis of aminopyrimidine and cyclic guanidine amino acids", Tetrahedron Letters, Aug. 21, 2013, vol. 54, No. 34, pp. 4526-4528, doi: 10.1016/j.tetlet.2013.06.066, available online Jun. 24, 2013.
Neises et al., "Simple Method for the Esterification of Carboxylic Acids", Angewandte Chemie, International Edition, Jul. 1978, vol. 17, No. 7, pp. 522-524, doi: 10.1002/anie.197805221.
Olson et al., "Vicinal Diamination of Alkenes under Rh-Catalysis", Journal of the American Chemical Society, Sep. 18, 2014, vol. 136, pp. 13506-13509, doi: 10.1021/ja506532h.
Parmar et al., "Defining the molecular structure of teixobactin analogues and understanding their role in antibacterial activities", Chemical Communications, Jan. 13, 2017, vol. 53, pp. 2016-2019, doi: 10.1039/C6CC09490B.
Parmar et al., "Efficient total syntheses and biological activities of two teixobactin analogues", Chemical Communication, Mar. 9, 2016, vol. 52, No. 36, pgs., doi: 10.1039/C5CC10249A.
Sanière et al., "Iminoiodane mediated aziridination of α-allylglycine: access to a novel rigid arginine derivative and to the natural amino acid enduracididine", Tetrahedron, Jul. 5, 2004, vol. 60, No. 28, pp. 5889-5897, doi: 10.1016/j.tet.2004.05.034, available online Jun. 9, 2004.
Sarabia et al., "Chemistry and biology of cyclic depsipeptides of medicinal and biological interest", Current Medicinal Chemistry, May 2004, vol. 11, pp. 1309-1332.
Steenbergen et al., "Daptomycin: a lipopeptide antibiotic for the treatment of serious Gram-positive infections", Antimicrobial Chemotherapu, 2005, vol. 55, pp. 283-288, doi: 10.1093/jac/dkh546.
Straus et al., "Mode of action of the new antibiotic for Gram-positive pathogens daptomycin: comparison with cationic antimicrobial peptides and lipopeptides", Biochim et Biophys Acta, Sep. 2006, vol. 1758, No. 9, pp. 1215-1223, doi: 10.1016/j.bbamem.2006.02.009, available online Mar. 3, 2006.
Tsuji et al., "Synthesis of Enduracididine, a Component Amino Acid of Antibiotic Enduracidin", Chemistry Letters, 1975, vol. 4, No. 12, pp. 1281-1284, doi: 10.1246/cl.1975.1281.
Von Nussbaum et al., "Multiple Attack on Bacteria by the New Antibiotic Teixobactin", Angew. Chem. Int. Ed., Feb. 13, 2015, vol. 54, pp. 2-5, doi: 10.1002/anie.201501440.
Welzel, "Syntheses around the Transglycosylation Step in Peptidoglycan Biosynthesis", Chemical Review, Mar. 1, 2005, vol. 105, pp. 4610-4660, doi: 10.1021/cr040634e.

(56) References Cited

OTHER PUBLICATIONS

White et al., "Contemporary strategies for peptide macrocyclization", Nature Chemistry, Jun. 23, 2011, vol. 3, pp. 509-524, doi: 10.1038/nchem.1062.

Wiegand et al., "Agar and broth dilution methods to determine the minimal inhibitory concentration (MIC) of antimicrobial substances", Nature Protocols, 2008, vol. 3, No. 2, pp. 163-175, doi: 10.1038/nprot.2007.521, published online Jan. 17, 2008.

Wright et al., "Antibiotics: An irresistible newcomer", Nature, Jan. 22, 2015, vol. 517, No. 7535, pp. 442-444, doi: 10.1038/nature14193.

Wu et al., "Synthesis and structure-activity relationship studies of teixobactin analogues", RSC Advances, Jan. 12, 2017, vol. 7, No. 4, pp. 1923-1926, doi: 10.1039/C6RA26567G.

Yang et al., "Elucidation of the Teixobactin Pharmacophore", ACS Chemical Biology, May 27, 2016, vol. 11, No. 7, 41 pgs., doi: 10.1021/acschembio.6b00295.

Yang et al., "X-ray crystallographic structure of a teixobactin analogue reveals key interactions of the teixobactin pharmacophore", Chemical Communication, Feb. 2017, vol. 53, pp. 2772-2775, doi: 10.1039/c7cc00783c.

Yang et al., "X-ray Crystallographic Structure of a Teixobactin Analogue Reveals Key Interactions of the Teixobactin Pharmacophore", Supplemental Information, 17 pgs., (Feb. 2017).

Extended European Search Report for European Application No. 17783359.7, Search completed Feb. 27, 2020, dated Mar. 12, 2020, 16 pgs.

Partial Supplementary European Search Report for European Application No. 17783359.7, Search completed Nov. 15, 2019, dated Nov. 26, 2019, 16 Pgs.

\* cited by examiner

FIG. 5A

Table 1. MIC of Teixobactin Homologues in µg/mL

| | Staphylococcus epidermidis ATCC 14990 | Streptococcus salivarius ATCC 13419 | Enterococcus durans ATCC 6056 | Bacillus subtilis ATCC 6051 | Escherichia coli ATCC 10798 |
|---|---|---|---|---|---|
| Arg$_{10}$-teixobactin | 1 | 1 | 4 | 2 | >32 |
| Lys$_{10}$-teixobactin | 0.25 | 0.5 | 1 | 0.5 | >32 |
| L-Thr$_8$,Arg$_{10}$-teixobactin | >32 | >32 | >32 | >32 | >32 |
| D-allo-Ile$_{11}$,Arg$_{10}$-teixobactin | 1 | 2 | 8 | 4 | >32 |
| oxa-Arg$_{10}$-teixobactin | >32 | >32 | >32 | >32 | >32 |
| est-Arg$_{10}$-teixobactin | 2 | 1 | 4 | 2 | >32 |
| short-Arg$_{10}$-teixobactin | >32 | >32 | >32 | >32 | >32 |
| lipobactin 1 | 4 | 4 | 8 | 1 | >32 |
| vancomycin | 0.5 | 0.5 | 0.5 | 1 | >32 |
| teixobactin | 0.08–0.3 various Staphylococcus | 0.02–0.15 various Streptococcus | 0.3–0.6 various Enterococcus | 0.02–0.6 various Bacillus | 25 E. coli$^+$ |

FIG. 5B

Table 2. MIC values of teixobactin homologues in μg mL⁻¹

| | Staphylococcus epidermidis ATCC 14990 | Streptococcus salivarius ATCC 13419 | Enterococcus durans ATCC 6056 | Bacillus subtilis ATCC 6051 | Escherichia coli ATCC 10798 |
|---|---|---|---|---|---|
| Arg10-teixobactin | 1 | 1 | 1 | 2 | >32 |
| Lipobactin 1 | 4 | 4 | 8 | 4 | >32 |
| Ac-Δ1-4,Arg10-teixobactin | >32 | >32 | >32 | >32 | >32 |
| Lys9,Arg10-teixobactin | >32 | >32 | >32 | >32 | >32 |
| Arg9,Lys10-teixobactin | >32 | >32 | >32 | >32 | >32 |
| Lys9,Arg10-teixobactin | 1 | 1 | 1 | 1 | >32 |
| Chg9,Arg10,Ohg11-teixobactin | 1 | 0.5 | 1 | 1 | >32 |
| Ala9,Arg10-teixobactin | 32 | 16 | >32 | 32 | >32 |
| D-Dap9,Arg10-teixobactin | 2 | 1 | 1 | 1 | >32 |
| Vancomycin | 0.5 | 0.5 | 0.5 | | >32 |
| Teixobactin | 0.06 | 0.03 | 0.5 | 0.06 | >32 |

ᵃ All teixobactin homologues were prepared and studied as the trifluoroacetate salts. The *Staphylococcus*, *Streptococcus*, *Enterococcus* and *Bacillus* species are non-pathogenic (BSL-1) Gram-positive bacteria. The *E. coli* serves as a Gram-negative control. Vancomycin and teixobactin serve as positive controls.

FIG. 5C

Table 3. MIC of Teixobactin Homologues in μg/mL

| | Staphylococcus epidermidis ATCC 14990 | Streptococcus salivarius ATCC 13419 | Enterococcus durans ATCC 6056 | Bacillus subtilis ATCC 6051 | Escherichia coli ATCC 10798 |
|---|---|---|---|---|---|
| Dap$_{10}$-teixobactin | 1 | 0.5 | 4 | 1 | >32 |
| Orn$_{10}$-teixobactin | 2 | 1 | 8 | 1 | >32 |
| His$_{10}$-teixobactin | >32 | >32 | >32 | >32 | >32 |
| Ala$_{10}$-teixobactin | 1 | 0.5 | 4 | 1 | >32 |
| Ala$_3$,Lys$_{10}$-teixobactin | 4 | 4 | 8 | 4 | >32 |
| lipobactin 1 (C$_{12}$H$_{23}$-Δ$_{1,5}$-Arg$_{10}$-teixobactin) | 16 | 8 | 8 | 32 | >32 |
| lipobactin 2 (C$_{14}$H$_{27}$-Δ$_{1,6}$-Arg$_{10}$-teixobactin) | >32 | | >32 | >32 | >32 |
| lipobactin 3 (C$_{16}$H$_{31}$-Δ$_{1,5}$-Lys$_{10}$-teixobactin) | 32 | | 4 | 16 | >32 |
| lipobactin 4 (C$_{16}$H$_{31}$-Δ$_{1,5}$-Arg$_{10}$-teixobactin) | 4 | 4 | 8 | 4 | >32 |
| lipobactin 5 (C$_{12}$H$_{23}$-Δ$_{1,5}$-Lys$_5$,Arg$_{10}$-teixobactin) | 32 | 32 | >32 | 32 | >32 |
| Ala$_3$,Lys$_{10}$-teixobactin | 4 | | 16 | 4 | >32 |
| D-Ala$_4$,Lys$_{10}$-teixobactin | 16 | 16 | >32 | | >32 |
| D-Ala$_3$,Lys$_{10}$-teixobactin | 4 | 4 | | | >32 |
| N-Propyl-Phe$_1$,Lys$_{10}$-teixobactin | >32 | >32 | >32 | >32 | >32 |
| Δ$_{1,4}$-Ile$_5$,n-octyl-gly$_8$,Arg$_{10}$-teixobactin | 2 | | 8 | 2 | >32 |
| D-Dap$_8$,Lys$_{10}$-teixobactin | 2 | | 4 | 2 | >32 |
| Lys$_{10}$,Phe$_{11}$-teixobactin | 32 | 8 | >32 | 32 | >32 |
| Lys$_9$,Lys$_{10}$,Lys$_{11}$-teixobactin | 32 | | >32 | >32 | >32 |
| Arg$_{10}$,Gly$_{11}$-teixobactin | >32 | 32 | >32 | >32 | >32 |
| N-Me-Ile$_2$,Lys$_{10}$-teixobactin | >32 | | >32 | >32 | >32 |
| N-Me-Ser$_7$,Lys$_{10}$-teixobactin | 2 | 1 | 8 | 4 | >32 |
| Lys(Mca)$_9$,Lys$_{10}$-teixobactin | 8 | 2 | 8 | 16 | >32 |
| Glu(PEG-Biotinyl)$_9$,Lys$_{10}$-teixobactin | >32 | >32 | >32 | >32 | >32 |
| Ala$_5$,Lys$_{10}$-teixobactin | 32 | 16 | >32 | 32 | >32 |

Arg₁₀-teixobactin

Lys₁₀-teixobactin

Orn₁₀-teixobactin lipobactin 1 short-Arg$_{10}$-teixobactin

Ac-Δ$_{1-5}$-Arg$_{10}$-teixobactin

L-Thr8,Arg10-teixobactin

D-*allo*-Ile11,Arg10-teixobactin seco-Arg10-teixobactin

*ent*-Arg10-teixobactin

Lys(Mca)₉,Lys₁₀-teixobactin

Glu(PEG-Biotinyl)₉,Lys₁₀-teixobactin

FIG. 24

ANTIMICROBIAL COMPOSITIONS

This is a U.S. national stage of Application No. PCT/US2017/027923 filed on Apr. 17, 2017, the disclosure of which is hereby incorporated by reference in its entirety. Application PCT/US2017/027923 claims priority to U.S. Provisional Application No. 62/322,911 filed on Apr. 15, 2016.

STATEMENT OF FEDERAL FUNDING

This invention was made with Government support under Grant No. Al121548 awarded by the National Institutes of Health. The Government has certain rights in the invention.

FIELD OF THE INVENTION

The present invention is directed to antimicrobial molecules, methods of synthesis and methods of treatment; and more particularly to antibiotics with activity against Gram-positive bacteria.

BACKGROUND OF THE INVENTION

Antimicrobial agents, including antibiotics, may either kill or inhibit the growth of bacteria. Often, the agents are used as antibiotics for the treatment or prevention of bacterial infections of hosts. A major complication in the medical and health field is antimicrobial resistance by pathogenic bacteria. The paucity of novel antimicrobial compounds exacerbates this problem, as health professional continue to rely on classical antibiotics. However, a research group recently discovered an antimicrobial agent, termed teixobactin (FIG. 1), that is not only very effective against Gram-positive bacteria, but also promises to avoid the development of resistance in bacteria (L. L. Ling, T. Schneider, A. J. Peoples, A. L. Spoering, I. Engels, B. P. Conlon, A. Mueller, T. F. Schäberle, D. E. Hughes, S. Epstein, M. Jones, L. Lazarides, V. A. Steadman, D. R. Cohen, C. R. Felix, K. A. Fetterman, W. P. Millett, A. G. Nitti, A. M. Zullo, C. Chen and K. Lewis, Nature, 2015, 517, 455-459, the disclosure of which is incorporated herein by reference). Specifically, teixobactin's antibacterial potency is believed to stem from its ability to inhibit cell wall synthesis in Gram-positive bacteria by binding to a highly conserved motif of lipid II (precursor of peptidoglycan) and lipid III (precursor of cell wall teichoic acid). Such mode of action is very promising for curbing bacterial drug resistance because peptidoglycans are much less prone to mutations than regular proteins. In addition, Gram-positive bacteria, which include MRSA and *Mycobacterium tuberculosis*, are especially sensitive to such mechanisms (also used by antibiotic vancomycin) because they are characterized by a thick peptidoglycan layer in the cell wall, access to which is facilitated by, also characteristic, absence of an outer membrane.

SUMMARY OF THE INVENTION

Embodiments of the invention are directed to antimicrobial compounds formed from teixobactin homologues and methods of their administration.

Many embodiments are directed to antimicrobial compound including:

a teixobactin homologue as set forth by:

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;

wherein position 1 is comprised of at least one of the following species selected from the group consisting of: a sequence of at least one natural or unnatural amino acid containing at least one hydrophobic side chain, and a hydrocarbon;

wherein the peptide ring has a stereochemistry that is configured such that the amide groups are aligned in a first direction, and such that the carbonyl groups of the peptide ring are aligned in a second direction opposite that of the first direction, and wherein the linkage X between position 8 and 11 is one of either an ester or an amide;

wherein positions 6 and 11 are comprised of either the same or different natural or unnatural amino acids, said amino acids each having a hydrophobic side chain;

wherein position 9 is comprised of any natural or unnatural amino acid; and wherein position 7 is comprised of serine or another natural or unnatural amino acids, said amino acid having a side chain hydroxyl group.

In other embodiments the position 10 amino acid is selected from the group of: allo-enduracididine, arginine, lysine, ornithine, 2,3-diaminopropionic acid, and histidine.

In still other embodiments the teixobactin homologue is selected from the group of: $Lys_{10}$-teixobactin, $Dap_{10}$-teixobactin, and $Orn_{10}$-teixobactin.

In yet other embodiments position 1 is selected from the group of: N-Me-D-$Phe_1$-$Ile_2$-$Ser_3$-D-$Gln_4$-D-allo-$Ile_5$, N-Me-D-$Phe_1$-$Ile_2$-$Ala_3$-D-$Gln_4$-D-allo-$Ile_5$, N-Me-D-$Phe_1$-$Ile_2$-$Ser_3$-D-$Ala_4$-D-allo-$Ile_5$, N-Me-D-$Phe_1$-$Ile_2$-$Ser_3$-D-$Gln_4$-D-$Ala_5$, N-Propyl-D-$Phe_1$-$Ile_2$-$Ser_3$-D-$Gln_4$-D-allo-$Ile_5$, N-Me-D-$Phe_1$-$Ala_2$-$Ser_3$-D-$Gln_4$-D-allo-$Ile_5$, $\Delta_{1-4}$-$Ile_5$, N-Me-D-$Ala_1$-$Ile_2$-$Ser_3$-D-$Gln_4$-D-allo-$Ile_5$, L-5F-$Phe_1$-$Ile_2$-$Ser_3$-D-$Gln_4$-D-allo-$Ile_5$, L-$Phe_1$-$Ile_2$-$Ser_3$-D-$Gln_4$-D-allo-$Ile_5$, 6 to 20 carbon long linear, cyclic, or branched alkyl, dodecanoyl, n-$C_{16}H_{31}$-noyl, and a PEG-derived group.

In still yet other embodiments the teixobactin homologue is one of: $Ala_3$,$Lys_{10}$-teixobactin, $\Delta_{1-5}$-$C_{12}H_{23}$-$Arg_{10}$-teixobactin, $\Delta_{1-6}$-$C_{12}H_{23}$-$Arg_{10}$-teixobactin, $\Delta_{1-5}$-$C_{16}H_{31}$-$Arg_{10}$-teixobactin, $\Delta_{1-5}$-$C_{12}H_{23}$-$Lys_9$,$Arg_{10}$, D-$Ala_4$,$Lys_{10}$-teixobactin, D-Ala$_5$,Lys$_{10}$-teixobactin, N-Propyl-Phe$_1$,Lys$_{10}$-teixobactin, N-Me-D-Ala$_1$,Lys$_{10}$-teixobactin, L-5F-Phe$_1$, Lys$_{10}$-teixobactin, L-Phe$_1$,Lys$_{10}$-teixobactin, $\Delta_{1-7}$-Arg$_{10}$-teixobactin, ent-Arg$_{10}$-teixobactin, D-Dap$_8$,Arg$_{10}$-teixobactin D-Dap$_8$,Lys$_{10}$-teixobactin, and, D-allo-Ile$_{11}$, Arg$_{10}$-teixobactin.

In still yet other embodiments one or both of positions 6 and 11 are selected from the group of: isoleucine and cyclohexylglycine.

In still yet other embodiments the compound is one of: Chg$_6$,Arg$_{10}$,Chg$_{11}$-teixobactin, Lys$_{10}$,Phe$_{11}$-teixobactin, Lys$_{10}$,Val$_{11}$-teixobactin, Lys$_{10}$,Leu$_{11}$-teixobactin.

In still yet other embodiments position 9 is selected from the group consisting of: alanine, an amino acid functionalized with a polyethylene glycol (PEG) derivative, Gln (PEG$_6$OMe), Lys(Mca)$_9$,Lys$_{10}$, an amino acid functionalized with biotin, an amino acid functionalized with a PEG derivative and biotin, Glu(PEG-Biotinyl)$_9$.

In still yet other embodiments the compound is one of: Lys$_9$,Lys$_{10}$-teixobactin, Lys$_9$,Arg$_{10}$-teixobactin, Lys(Mca)$_9$, Lys$_{10}$-teixobactin, Glu(PEG-Biotinyl)$_9$,Lys$_{10}$-teixobactin, Lys$_9$,Lys$_{10}$,Lys$_{11}$-teixobactin, Ile$_9$,Arg$_{10}$-teixobactin.

In still yet other embodiments the hydrophobic compound at position 1 is a hydrocarbon.

Many other embodiments are directed to a biological probe including: a teixobactin homologue as set forth by:

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;

wherein position 1 is comprised of at least one of the following species selected from the group consisting of a sequence of at least one natural or unnatural amino acid comprising at least one hydrophobic side chain, a hydrocarbon;

wherein the peptide ring has a stereochemistry that is configured such that the amide groups are aligned in a first direction, and such that the carbonyl groups of the peptide ring are aligned in a second direction opposite that of the first direction, and wherein the linkage X between position 8 and 11 is one of either an ester or an amide;

wherein positions 6 and 11 are comprised of either the same or different natural or unnatural amino acids, said amino acids each having a hydrophobic side chain;

wherein position 9 is comprised of any natural or unnatural amino acid having a biological marker attached thereto; and wherein position 7 is comprised of serine or another natural or unnatural amino acids, said amino acid having a side chain hydroxyl group.

Still many other embodiments are directed to a prodrug including: a teixobactin homologue as set forth by:

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;

wherein position 1 is comprised of at least one of the following species selected from the group consisting of a sequence of at least one natural or unnatural amino acid comprising at least one hydrophobic side chain, a hydrocarbon;

wherein the peptide ring has a stereochemistry that is configured such that the amide groups are aligned in a first direction, and such that the carbonyl groups of the peptide ring are aligned in a second direction opposite that of the first direction, and wherein the linkage X between position 8 and 11 is one of either an ester or an amide;

wherein positions 6 and 11 are comprised of either the same or different natural or unnatural amino acids, said amino acids each having a hydrophobic side chain;

wherein position 9 is comprised of any natural or unnatural amino acid; and wherein position 7 is comprised of an esterified serine or another natural or unnatural amino acids, said amino acid having a side chain hydroxyl group, having a solubilizing functionality attached thereto.

In other embodiments the esterified serine is one of either: Ser-O-(PEG derivative) and Ser-O-(amino acid)$_n$-NH$^{3+}$.

Yet other embodiments are directed to methods of treating a microbial infection including:

administering a therapeutically effective amount of a teixobactin homologue to a patient having an microbial infection;

wherein the teixobactin homologue is set forth by:

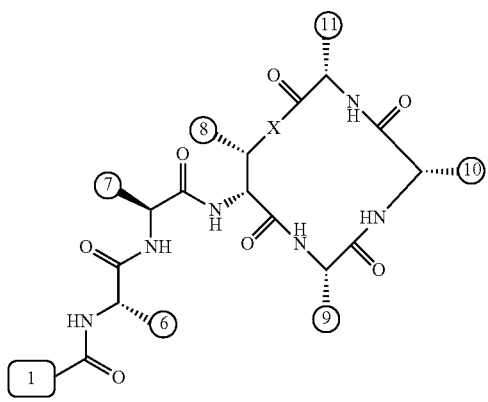

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;
wherein position 1 is comprised of at least one of the following species selected from the group consisting of a sequence of at least one natural or unnatural amino acid comprising at least one hydrophobic side chain, a hydrocarbon;
wherein the peptide ring has a stereochemistry that is configured such that the amide groups are aligned in a first direction, and such that the carbonyl groups of the peptide ring are aligned in a second direction opposite that of the first direction, and wherein the linkage X between position 8 and 11 is one of either an ester or an amide;
wherein positions 6 and 11 are comprised of either the same or different natural or unnatural amino acids, said amino acids each having a hydrophobic side chain;
wherein position 9 is comprised of any natural or unnatural amino acid; and
wherein position 7 is comprised of serine or another natural or unnatural amino acids, said amino acid having a side chain hydroxyl group.

Still yet other embodiments are directed to an antimicrobial medicinal compound including:
a therapeutically effective amount of a teixobactin homologue set forth by:

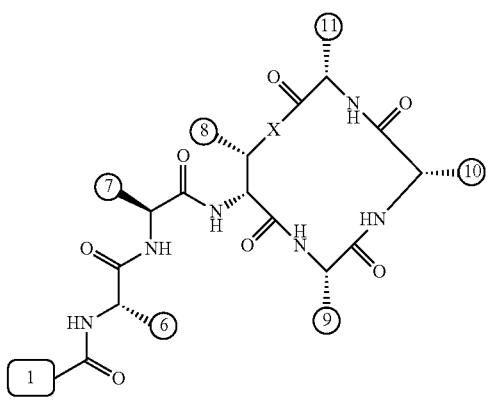

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;
wherein position 1 is comprised of at least one of the following species selected from the group consisting of a sequence of at least one natural or unnatural amino acid comprising at least one hydrophobic side chain, a hydrocarbon;
wherein the peptide ring has a stereochemistry that is configured such that the amide groups are aligned in a first direction, and such that the carbonyl groups of the peptide ring are aligned in a second direction opposite that of the first direction, and wherein the linkage X between position 8 and 11 is one of either an ester or an amide;
wherein positions 6 and 11 are comprised of either the same or different natural or unnatural amino acids, said amino acids each having a hydrophobic side chain;
wherein position 9 is comprised of any natural or unnatural amino acid; and
wherein position 7 is comprised of serine or another natural or unnatural amino acids, said amino acid having a side chain hydroxyl group.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein:
FIGS. 5A, 5B, and 5C are tables of MIC of teixobactin homologues in accordance with embodiments of the application.

FIG. 24 is a chemical structure drawing of $Ala_7$,$Arg_{10}$-teixobactin in accordance with embodiments of the application.

DETAILED DISCLOSURE

The embodiments of the invention described herein are not intended to be exhaustive or to limit the invention to precise forms disclosed. Rather, the embodiments selected for description have been chosen to enable one skilled in the art to practice the invention.

Turning now to the diagrams and figures, antimicrobial molecules, their synthesis and use as antimicrobial treatments are described. In some embodiments, the antimicrobial compounds are teixobactin analogues. Other embodiments are directed to methods of synthesizing antimicrobial teixobactin analogues. In some other embodiments, antibiotic therapeutics comprising antimicrobial teixobactin analogues are provided, along with methods of and formulations for treating microbial infections using such antimicrobial teixobactin analogues. In various other embodiments, prodrugs formed using esterified forms of antimicrobial teixobactin analogues may be provided.

Figure 2:
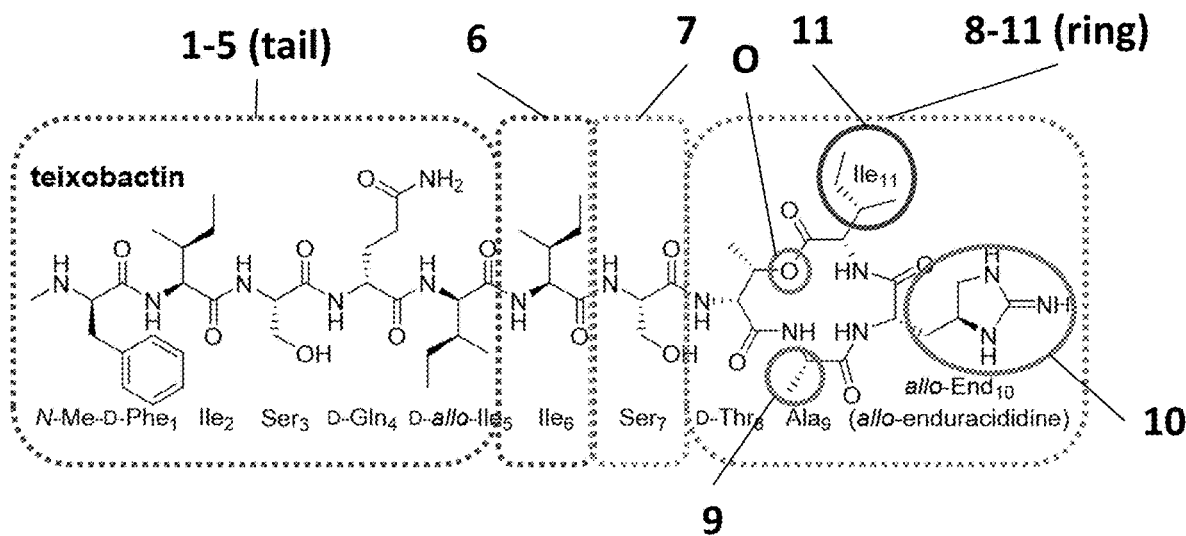
FIG. 2 is a schematic depiction of teixobactin and its chemical and structural features in accordance with embodiments of the application.

In many embodiments, the teixobactin analogues are undecapeptides of eleven natural and/or unnatural amino acids of variable stereochemistry (the amino acids are labelled herein numerically as residues or positions 1 through 11), as shown in FIG. 2.

In some embodiments, the N-terminal amino acids of the undecapeptide teixobactin analogues (e.g., positions 1-5 in FIG. 2, although the number and type of N-terminal amino acids may vary) are replaced with a hydrophobic group. In other embodiments, the hydrophobic group is a hydrocarbon. In other embodiments, the hydrocarbon is a 6 to 20 carbon long linear alkyl chain. In some other embodiments the alkyl group is cyclic or branched. In yet other embodiments, the hydrocarbon is a dodecanoyl group. In yet other embodiments, the N-terminal amino acids are replaced with a lipid compatible solubilizing group. In still other embodiments, the solubilizing group is a polyethylene glycol (PEG) derivative. In still yet other embodiments, the PEG derivative is Me(OCH$_2$CH$_2$)$_3$CO—. In still yet other embodiments, the PEG functionality is Me(OCH$_2$CH$_2$)$_4$CO—. In some other embodiments, the N-terminus of the teixobactin analogues interacts with the phospholipid membrane of Gram-positive bacteria.

In many embodiments the residues at positions 6 and 9 of the teixobactin analogues are configured to have a hydrophobic nature. In many other embodiments, the residues at positions 6 and 11 are either the same or different natural or unnatural amino acids with hydrophobic side chains. In some of the embodiments, the amino acids at positions 6 and 11 may be isoleucine and/or cyclohexylglycine.

In many embodiments the serine residue at position 7 is preserved in the teixobactin analogues. In some embodiments the residue at position 7 is replaced with a natural or unnatural amino acid with a hydrogen bond capable side chain. In yet some other embodiments the serine or any similar natural or unnatural amino acid at position 7 is esterified with a temporary, properties enhancing functionality. In some embodiments the properties enhancing functionality is a solubilizing PEG derivative group. In some embodiments the residue used for temporary esterification is serine residue 3, if available. In many embodiments the ester bond at residue 7 or 3 is broken in the patient's blood stream, with the full reinstitution of the pre-esterification antimicrobially active compound.

In many embodiments the alanine residue at position 9 is altered to introduce a properties enhancing functionality or group. In some embodiments the residue at position 9 is functionalized with a solubilizing group. In some other embodiments the solubilizing group is water solubilizing PEG derivative group. In yet other embodiments the residue 9 is mutated to Gln-(PEG$_6$OMe), the derivative of Glu in which the side chain has been coupled to H$_2$NCH$_2$CH$_2$(OCH$_2$CH$_2$)$_5$OMe. In still other embodiments position 9 residue is functionalized with a traceable label to enable mechanistic or other studies of teixobactin and its analogues. In still yet other embodiments position 9 residue is functionalized with biotin or coumarin. In still yet other embodiments the teixobactin analogues with a position 9 mutation are Lys(Mca)$_9$,$Lys_{10}$-teixobactin and Glu(PEG-Biotinyl)$_9$, $Lys_{10}$-teixobactin.

In some embodiments, the side chain of position 10 residue interacts with the extracellular peptidoglycan of Gram-positive bacteria. In other specific embodiments, an amine group of the side chain of the amino acid at position 10 may interact with an anionic pyrophosphate group of the bacterial peptidoglycan. In many embodiments, the residue at position 10 has a guanidinium group or its cyclic analogue. In some of the embodiments, residue 10 may include allo-enduracididine, arginine, lysine, ornithine, 2,3-diaminopropionic acid, or histidine. In alternative embodiments residue 10 may confer solubility by the use of a PEGylated lipid.

In many embodiments, the residues 8-11 form a depsipeptide ring. In some embodiments the 8-11 residue macrocycle has amide (peptide) connections only. In some other embodiments, the peptide backbone amides of the ring formed by residues 8-11 may interact with an anionic pyrophosphate group of the bacterial peptidoglycan.

In some embodiments, the teixobactin analogue is lipobactin. In other embodiments, the teixobactin analogue is selected from the group of: $Lys_{10}$-teixobactin, D-allo-$Ile_{11}$, $Arg_{10}$-teixobactin, $Arg_{10}$-teixobactin, ent-$Arg_{10}$-teixobactin, D-$Dap_8$,$Arg_{10}$-teixobactin, $Lys_9$,$Lys_{10}$-teixobactin, and $Dap_{10}$-teixobactin Many other embodiments are directed to administering embodiments of teixobactin analogues to hosts that may have a pathogenic bacterial infection. Even other embodiments are directed to medicinal formulations formed using a teixobactin analogue. Some such formulations may include conjoining teixobactin analogues with an excipient. In even some other embodiments, the teixobactin analogues are stored or administered in a suitable buffer.

The embodiments of the invention described herein are not intended to be exhaustive or to limit the invention to precise forms disclosed. Rather, the embodiments selected for description have been chosen to enable one skilled in the art to practice the invention.

Structure and Function of Teixobactin

Figure 1:
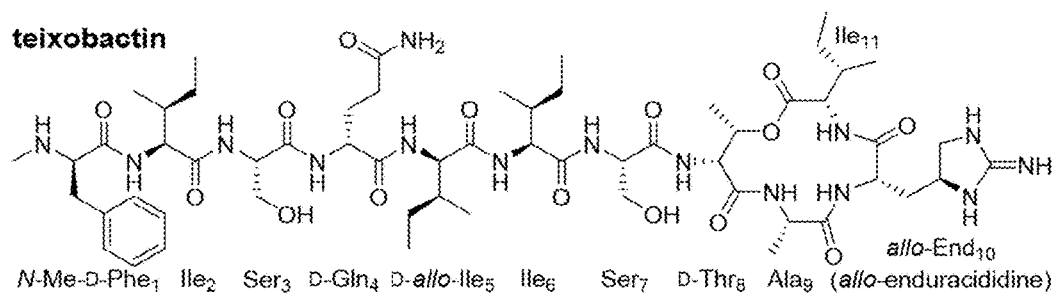
FIG. 1 is a chemical structure drawing of teixobactin in accordance with the prior art.
Figure 3:
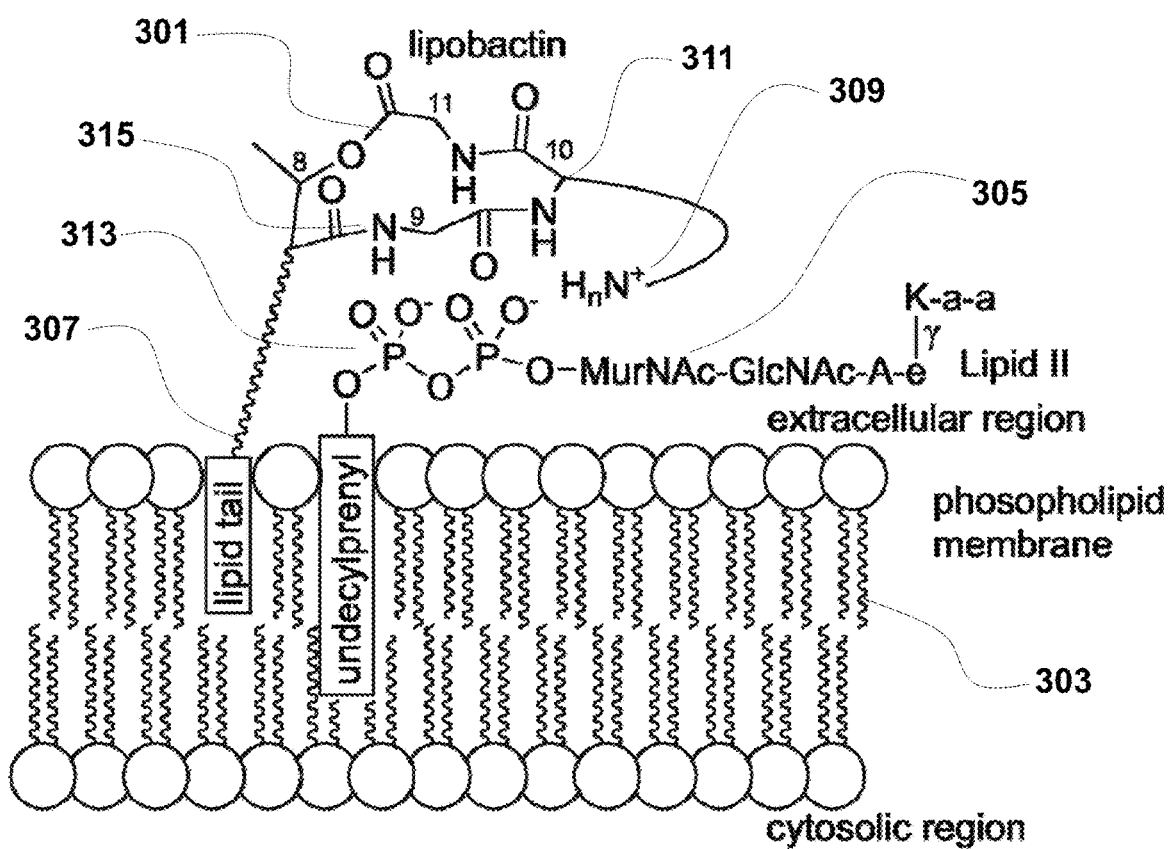
FIG. 3 is a schematic of the mechanism of interaction between lipobactin and Gram-positive bacteria, in accordance with embodiments of the application.

The antibiotic teixobactin, first reported in 2015, is a nonribosomal undecapeptide containing a macrocyclic depsipeptide group (FIG. 1). As such, it contains four D-amino acids and seven L-amino acids, wherein the C-terminal's $Ile_{11}$ is cyclized onto the side chain of D-$Thr_8$ to form a 13-membered lactone. In addition, residue 10 of teixobactin is a rare nonproteinogenic amino acid, L-allo-enduracididine (allo-$End_{10}$), which is a cyclic analogue of arginine. It has been postulated that, similar to the action mechanism of known antibiotic vancomycin, teixobactin's efficacy stems from its ability to inhibit cell wall formation in Gram-positive bacteria by binding to the wall's lipid II (via prenyl-pyrophosphate-GlcNAc region) and related peptidoglycan precursors (FIG. 3). Therefore, since these binding targets are highly conserved in bacteria and cannot easily mutate to impart drug resistance, teixobactin-based antibiotics offer great promise to the efforts directed against rising resistance in pathogens such as methicillin-resistant *Staphylococcus aureus* (MRSA).

Several distinct chemical and structural features of teixobactin, while potentially imparting antibacterial effectiveness, also make this peptide extremely difficult and expensive to produce, especially to scale. Therefore, the ongoing efforts towards both the efficient synthetic routes for production of teixobactin and elucidation of its pharmacophore with the intent to obtain equally or even more potent yet easy to synthesize homologues are quite extensive. To date, such efforts have produced several reports of the total syntheses of teixobactin (see, e.g., K. Jin, L. H. Sam, K. H. Laam Po, D. Lin, E. H. Ghazvini Zadeh, S. Chen, Y. Yuan and X. Li, Nat. Commun., 2016, 7, 12394; and A. M. Giltrap, L. J. Dowman, G. Nagalingam, J. L. Ochoa, R. G. Linington, W. J. Britton and R. J. Payne, Org. Lett., 2016, 18, 2788; the disclosures of which are incorporated herein by reference), as well as a report describing the synthesis of the teixobactin's cyclic depsipeptide ring. (See, e.g, S. Dhara, V. B. Gunjal, K. L. Handore and D. S. Reddy, Eur. J. Org. Chem., 2016, 4289, the disclosures of which is incorporated herein by reference.) In addition, a 10-step synthesis of allo-enduracididine component of teixobactin suitable for preparing gram-quantities has also been reported. (See. e.g., W. Craig, J. Chen, D. Richardson, R. Thorpe and Y. Yuan, Org. Lett., 2015, 17, 4620, the disclosures of which is incorporated herein by reference.) However, the exact roles the various chemical and structural functionalities play in the teixobactin's antimicrobial efficacy remain to be established.

Based on the available information concerning the teixobactin analogues, the following structural binding between teixobactin and the Lipid II of Gram-positive bacteria is proposed in accordance with embodiments. As shown in FIG. 3, teixobactin or its active analogue (301) interacts with both the phospholipid membrane (303) and the extracellular peptidoglycan molecules (305). Specifically, the hydrophobic N-terminal region (307) of the antibiotic compound (e.g. dodecanoyl group) interacts with the hydrophobic phospholipid membrane (303). In addition, the macrocyclic peptide backbone amides (315) may interact with the pyrophosphate groups of peptidoglycans (313) via hydrogen bonding. Furthermore, the side chain of residue 10 (309) may also beneficially interact with bacterial cell wall peptidoglycans, including via peptidoglycan pyrophosphate groups (313).

Antimicrobial Teixobactin Analogues

Figure 4A:
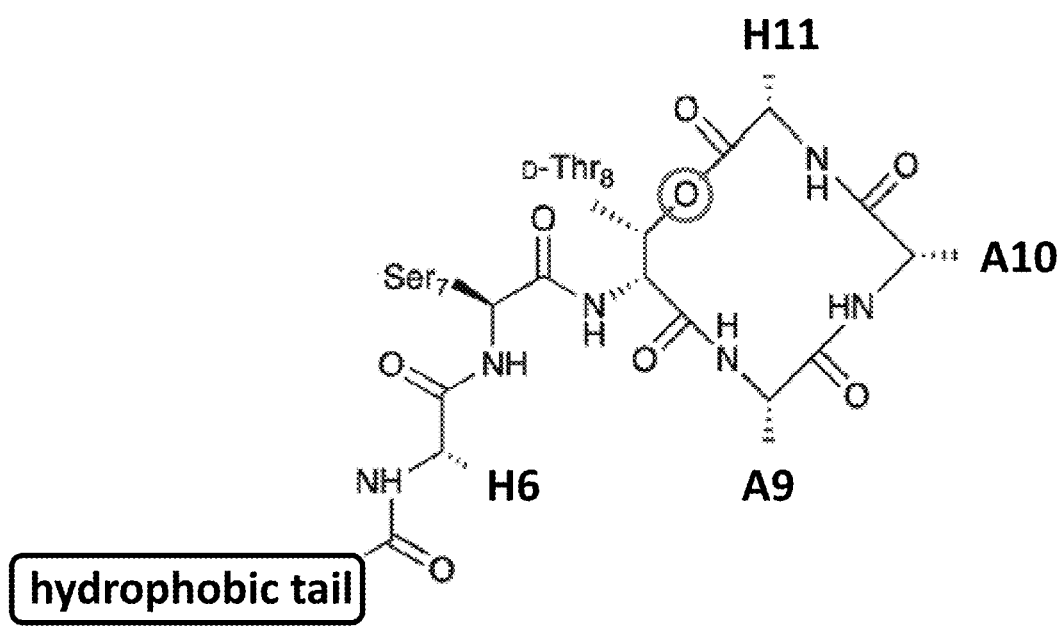
FIG. 4A is a schematic depiction of teixobactin and its chemical and structural features in accordance with embodiments of the application.

Accordingly, many embodiments of the invention are directed to teixobactin analogues having antibacterial properties and methods of manufacture thereof. Specifically, embodiments are directed to analogues of teixobactin having specific substitutions that have equivalent or stronger antimicrobial efficacy, but that are more chemically accessible. In many embodiments (as highlighted in FIG. 4A reproduced below), these features include:

- the presence of a 13-membered peptide ring, its composition (particularly at positions 9, 10, and 11), and its stereochemistry;
- the presence of a hydrogen bond capable serine moiety at position 7;
- the presence of a hydrophobic functionality at positions 6 and 11;
- the presence of a hydrophobic tail composed of residues 1-5.

Accordingly, an antibacterial compound based on teixobactin (FIG. 1) in accordance with embodiments of the invention may comprise the molecule as illustrated in the molecular schematic:

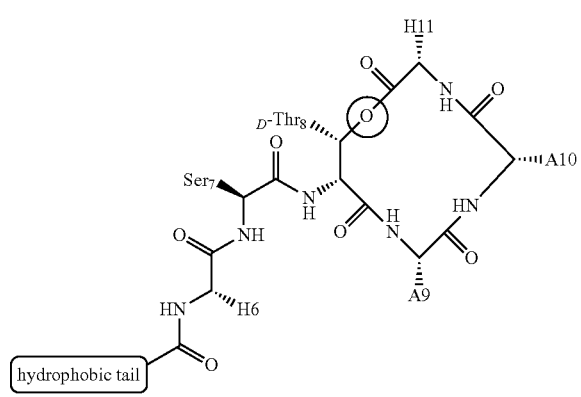

where A10 in many embodiments may be a natural or unnatural amino acid selected from arginine, lysine, ornithine, 2,3-diaminopropionic acid, or histidine, or an amino acids with one of the following: a side chain capable of hydrogen bonding, a hydrogen, hydrophobic or hydrophilic side chains, or PEG derivative;

where the hydrophobic tail comprises residues 1-5 comprising any number of natural or unnatural amino acids with hydrophobic side chains, or any other hydrophobic functionality chosen from hydrocarbons, including 6 to 20 carbon long alkyls, or other hydrocarbons of any length or structure, including dodecanoyl, or PEG;

where the macrocyclic peptide consisting of residues 8-11 having a stereochemistry such that the ring's amide groups point in the same direction, which is the opposite of the direction in which the ring's carbonyl groups point, and where the macrocycle's linkage between residues 8 and 11 is either an ester or an amide;

where H6 and H11 are either same or different natural or unnatural amino acids with a hydrophobic side chain, including isoleucine (Ile) and cyclohexylglycine (Chg);

where A9 is any natural or unnatural amino acid with any suitable side chain, including alanine; polyethylene glycol (PEG) derivatives, such as PEG-containing amino acid, such as $Gln(PEG_6OMe)$, the derivative of Glu in which the side chain has been coupled to $H_2NCH_2CH_2(OCH_2CH_2)_5OMe$; and/or biotin and other biological labels/markers; and where residue 7 is serine or any similar natural or unnatural amino acid with a hydrogen bond capable side chain functionality, and where residue 7 can be esterified with PEGs or the like to impart solubility to the peptide in a pro-drug fashion to convert in blood stream once in the body.

Figure 4B:
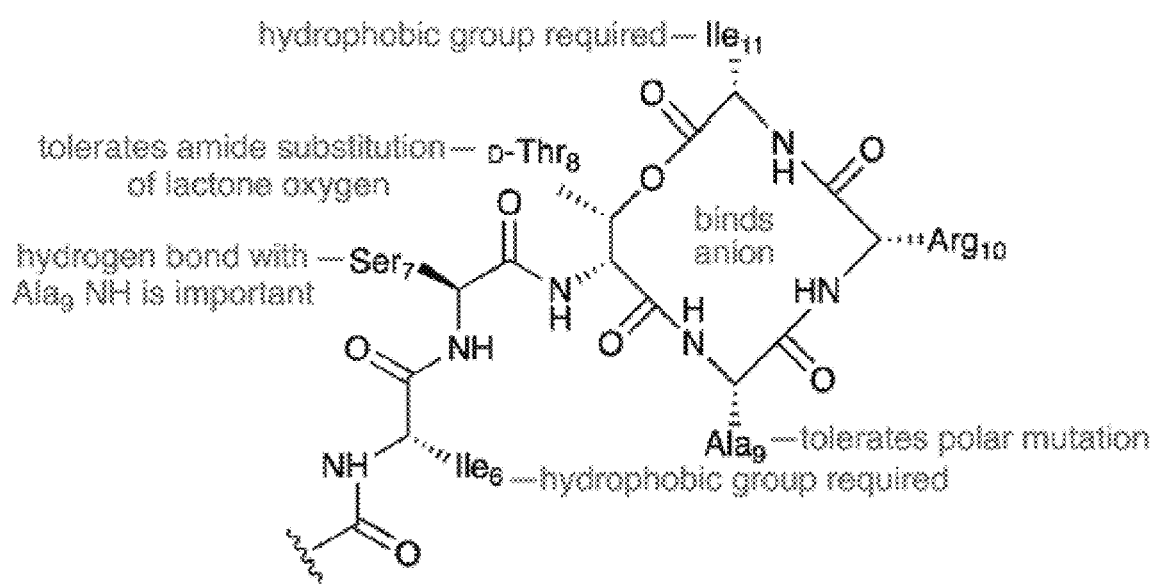
FIG. 4B is an illustrative schematic depiction of teixobactin and its chemical and structural features in accordance with embodiments of the application.

FIG. 4B summarizes the key features of teixobactin to be considered in the design of new chemically accessible compounds with similar or enhanced antibacterial efficacy according to embodiments. Specifically, these features include a 13-membered peptide ring in which the amide and ester groups of residues 8-11 align, such that to allow the creation of an anion binding cavity. In addition, the hydrophobic side chains at positions 6 and 11 are required for activity, whereas that at position 9 is not, which invites modifications at position 9 as needed to enhance compounds' properties. In addition, the hydrogen bond capable $Ser_7$ is also important for activity and the teixobactin pharmacophore tolerates the amide substitution of lactone oxygen in the ring. In accordance with these specifications, a variety of different teixobactin analogues have been proposed for use in a variety of applications, including, for example, antimicrobial therapeutic formulations, biolabeling applications and prodrugs.

Antibiotic Therapeutics & Treatments

Some embodiments of the invention are directed to antimicrobicals (e.g., antibiotics) targeted at, for example, Gram-positive bacteria, and methods of treatment using such antimicrobials. The methods may include identifying a subject having, developing, or at-risk of developing Gram-positive bacterial infection and administering a therapeutically effective amount of a teixobactin analogue (as described above), e.g., lipobactin. Identification of bacterially infected hosts, or hosts that are at-risk of a bacterial infection can be performed in a number of ways, including but not limited to, identification by phenotypic symptoms, e.g. inflammation; identification by lab testing, e.g. bacterial; or a well-known at-risk action or behavior, e.g. surgery.

In some embodiments, the teixobactin analogues (described above) may be administered in a therapeutically effective amount as part of a course of treatment. As used in this context, to "treat" means to ameliorate at least one symptom of a bacterial infection. A therapeutically effective amount can be an amount sufficient to prevent the onset of symptoms related to a bacterial infection or to decrease the severity of one or more symptoms. In some embodiments, a therapeutically effective amount inhibits or reduces pathogenic bacterial growth in a host. In other embodiments, a therapeutically effective amount is an amount capable of killing pathogenic bacteria. In more embodiments, a therapeutically effective amount is an amount to reduce inflammation, e.gs. lymphocyte accumulation, lymphocyte activation, or cytokine secretion. In some other embodiments, a therapeutically effective amount is an amount capable of inhibiting bacterial growth in culture.

Dosage, toxicity and therapeutic efficacy of the compounds can be determined, e.g., by standard pharmaceutical procedures in cell cultures or experimental animals, e.g., for determining the MIC (minimum inhibitory concentration that will inhibit visible growth of an organism), the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the microbial culture assays, tissue culture assays and animal studies can be used in formulating a range of dosage for use in humans or other hosts. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. Such information can be used to more accurately determine useful doses in a host to receive antibiotics.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of infection or symptoms of an infection. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

In some embodiments, one could infer, based on the mode of administration, the vehicle of administration, the timing of administration, the type of infection and/or the desired result, the appropriate titer, volume, or concentration to administer or inject. Likewise, in many embodiments, the appropriate dose for a human infected host may be calculated from a clinical trial or a study in mouse, macaque, human or any other suitable animal.

In such embodiments, it will be understood that any teixobactin analogue as described in the application, either based on structural components or exemplified embodiments, could be used to treat bacterial infections. Examples of teixobactin analogues that could be used in some embodiments include, but are not limited to, lipobactin, $Lys_{10}$-teixobactin, $Arg_{10}$-teixobactin, derivatives thereof, and enantiomers thereof. Likewise, in other embodiments, it will be understood that any form vehicle or excipient in conjunction with teixobactin analogues could be used.

Evaluation of these antibiotics can be undertaken using any suitable technique, such as for example, application to a test sample, e.g., a cell or living tissue or organ, for evaluation. In a cultured or primary tissue for example, the ability of the test compound to suppress bacterial infection may be evaluated. Methods for evaluating each teixobactin analogue are well-known in the art.

Teixobactin analogues in accordance with structure described or exemplified by embodiment can be considered a candidate therapeutic. Candidate teixobactin analogues can be converted into an antibiotic. Furthermore, the antibiotics containing the teixobactin analogues may then be appropriately conjoined with a vehicle or excipient. The therapeutics can be stored in the appropriate formulation buffer capable of maintaining potency during shelf-life. Likewise, administration of the therapeutic can be performed in any suitable buffer for the procedure.

EXEMPLARY EMBODIMENTS

The following sections set forth certain selected embodiments related to the above disclosure. It will be understood that the embodiments presented in this section are exemplary in nature and are provided to support and extend the broader disclosure, these embodiments are not meant to confine or otherwise limit the scope of the invention.

The antibiotic activity of $Arg_{10}$-teixobactin and homologues was investigated in minimum inhibitory concentration (MIC) assays against four types of Gram-positive bacteria, as well as control substances, in order to elucidate the importance of various functionalities within teixobactin analogues and guide the rational design of new antimicrobial compounds (as summarized in Tables 1, 2 and 3 (FIGS. 5A, 5B, and 5C respectively). These MIC studies used vancomycin as a positive control and the Gram-negative bacterium *E. coli* as a negative control.

Example 1: Teixobactin Homologues with Position 10 Substitutions

Figure 6:
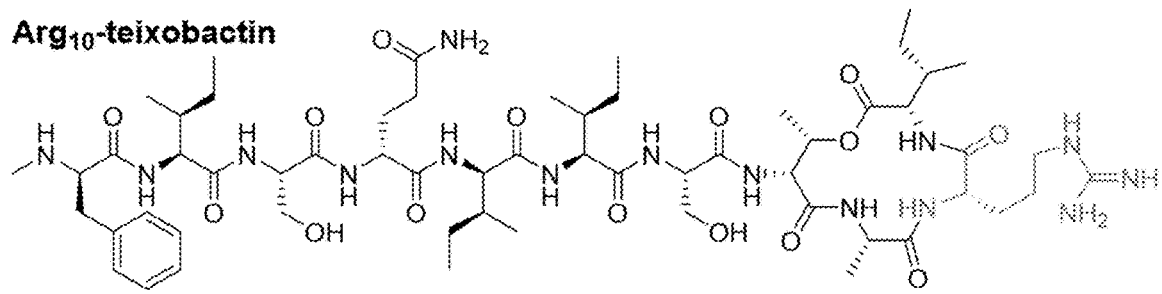
FIG. 6 is a chemical structure drawing of $Arg_{10}$-teixobactin in accordance with the prior art.

In many embodiments of the invention L-allo-enduracididine at position 10 (allo-$End_{10}$) of teixobactin and its analogues is replaced with other functionalities without significant loss of antimicrobial activity. allo-$End_{10}$ is a rare and commercially unavailable amino acid, which requires cumbersome multistep syntheses to produce. Therefore, a homologue in which allo-$End_{10}$ is substituted with a simpler, less expensive moiety without significant loss of overall peptide function is highly desirable in making usable antimicrobial compounds. One obvious substitution candidate is allo-enduracididine's acyclic analogue arginine, which is a common amino acid. Consequently, several research groups have reported structure-activity relationship studies of $Arg_{10}$-teixobactin (FIG. 6) and related homologues in which arginine is used as a surrogate for allo-enduracididine. (See, e.g. Y. E. Jad, et al., Org. Lett., 2015, 17, 6182; A. Parmar, et al., Chem. Commun., 2016, 52, 6060; H. Yang, K. H. Chen and J. S. Nowick, ACS Chem. Biol., 2016, 11, 1823; S. A. H. Abdel Monaim, Y, et al., RSC Adv., 2016, 6, 73827; S. A. H. Abdel Monaim, et al., ACS Omega, 2016, 1, 1262; C. Wu, et al., RSC Adv., 2017, 7, 1923; A. Parmar, et al., Chem. Commun., 2017, 53, 2016; the disclosures of which are incorporated herein by reference.) Overall, these studies report that $Arg_{10}$-teixobactin is about an order of magnitude less active against Gram-positive bacteria than teixobactin in minimum inhibitory concentration (MIC) assays.

Figure 7:
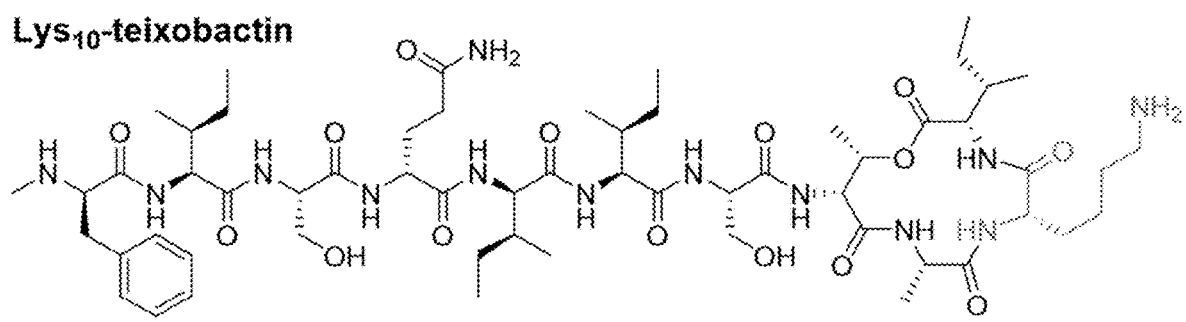
FIG. 7 is a chemical structure drawing of $Lys_{10}$-teixobactin in accordance with embodiments of the application.
Figure 8:
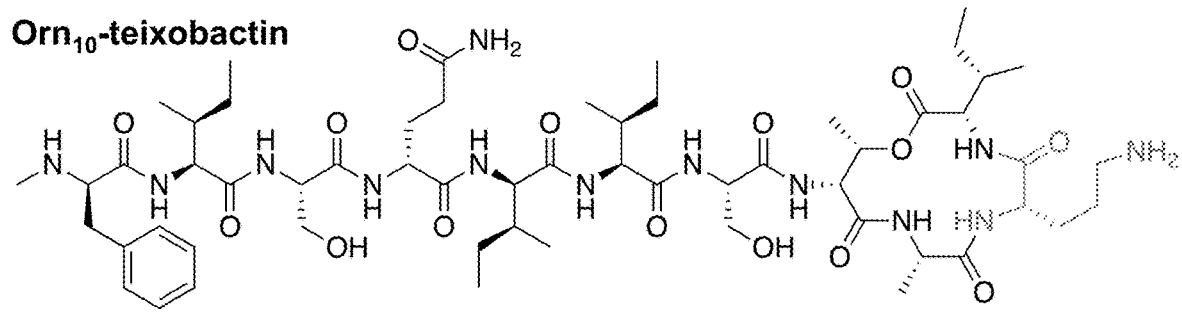
FIG. 8 a chemical structure drawing of $Orn_{10}$-teixobactin in accordance with embodiments of the application.

Tables 1-3 (FIGS. 5A-C) summarize the MIC assay results for some teixobactin analogues prepared according to the embodiments of the invention and compare them to native teixobactin, as well as known homologue $Arg_{10}$-teixobactin. To this end, $Arg_{10}$-teixobactin prepared according to the embodiments of the current invention demonstrates MIC values of 1-4 µg/mL against the four Gram-positive bacteria studied. These values, which are consistent with previously reported data for $Arg_{10}$-teixobactin, indicate that such position 10 substitution lowers teixobactin activity slightly, by only about an order of magnitude. However, unexpectedly, $Lys_{10}$-teixobactin (FIG. 7), produced by the substitution of position 10 allo-$End_{10}$ for lysine according to some embodiments of this invention, yielded MIC values 2-4 times lower than those reported for $Arg_{10}$-teixobactin in prior art. Although the MIC values presently measured for $Lys_{10}$-teixobactin were slightly higher than those reported for teixobactin, they are comparable to those of vancomycin, which is a well-established antibiotic drug, and is believed to have a similar to teixobactin's mechanism of antimicrobial action (Table 1). In addition, other position 10 substituted teixobactin homologues, such as ornithine substituted $Orn_{10}$-teixobactin (FIG. 8), were tested and demonstrated excellent to satisfactory antimicrobial activity (Table 3). Together, these findings indicate that the challenging enduracididine group at position 10 is not necessary for teixobactin's activity and that the proposed teixobactin homologues lacking allo-enduracididine are comparably potent.

Example 2: Residues 1-5 Tail of Teixobactin and Analogues (the Hydrophobic Tail)

Figure 9:
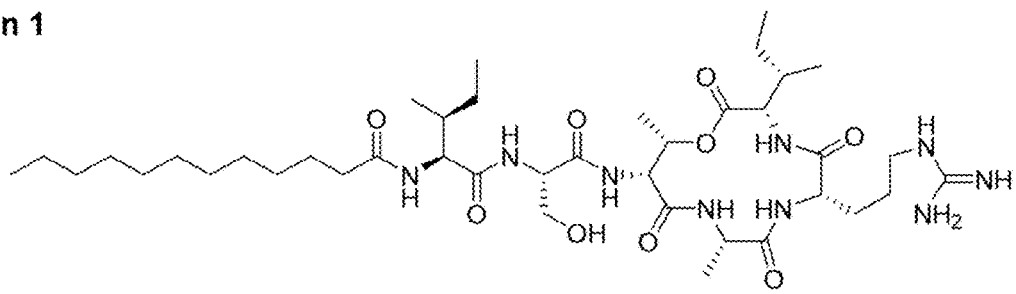
FIG. 9 is a chemical structure drawing of lipobactin 1 in accordance with embodiments of the application.
Figure 10:
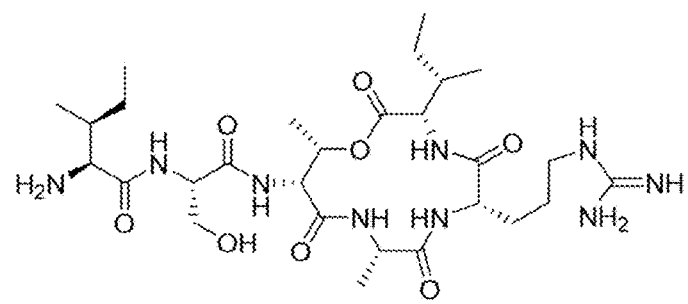
FIG. 10 is a chemical structure drawing of short-$Arg_{10}$-teixobactin in accordance with embodiments of the application.
Figure 11:
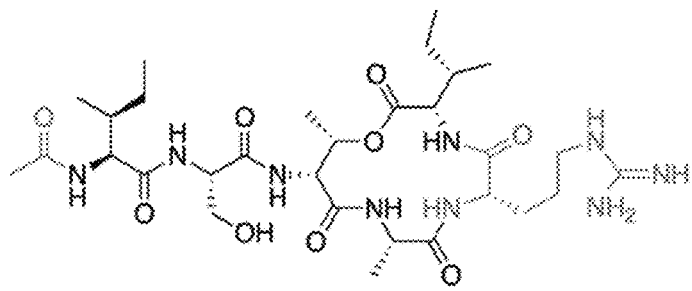
FIG. 11 is a chemical structure drawing of Ac-$\Delta_{1-5}$-$Arg_{10}$-teixobactin in accordance with embodiments of the application.

In some embodiments of the teixobactin analogues, hydrophobic residues 1-5 are replaced with a simple alkyl chain to yield dodecanoyl-$\Delta_{1-5}$-$Arg_{10}$-teixobactin (referred to as "lipobactin 1" herein, as shown in FIG. 9). This substitution was motivated by the investigation of the roles of the hydrophobic residues N-Me-D-Phe, Ile, and D-allo-Ile at positions 1, 2, and 5 according to the embodiments of the invention. Specifically, it was postulated that these hydrophobic moieties, collectively, form a lipid tail (307) that helps anchor teixobactin to the plasma membrane (303), which, in turn, is composed of phospholipids and, thus, enhances peptide's activity against the bacterial cell walls (as shown in FIG. 3). To this end, residues 1-5 were, first, completely truncated to produce short-$Arg_{10}$-teixobactin (FIG. 10) according to one embodiment of the invention, which proved to be inactive against any of the assessed bacterial cultures (MIC>32 µg/mL, Table 1). In addition, an acetylated version of the short teixobactin analogue, Ac-$\Delta_{1-5}$-$Arg_{10}$-teixobactin (FIG. 11), was prepared according to another embodiment and also proved inactive, although it was successfully used in the crystallization studies of teixobactin homologues. On the other hand, replacing teixobactin's residues 1-5 with a hydrophobic dodecanoyl group according to other embodiments of the invention yielded dodecanoyl-$\Delta_{1-5}$-Arg$_{10}$-teixobactin (or lipobactin 1, FIG. 9) with measured activity close to that of Arg$_{10}$-teixobactin (Tables 1-3). In yet another embodiment, substituting serine residue at position 3 for hydrophobic alanine diminished the activity of position 10 lysine analogue (Ala$_3$,Lys$_{10}$-teixobactin) only very slightly (Table 3). These findings, together, confirm the importance of the hydrophobicity of the N-terminal tail in teixobactin and homologues and allow for the development of compounds, in accordance with embodiments with enhanced pharmacological properties.

In addition, in some embodiments of the invention the water-solubility of teixobactin derivatives can potentially be manipulated without the loss of activity by the use of solubilizing functionalities that are also lipid compatible. In some embodiments PEG groups could be installed in place of the residues 1-5 of the hydrophobic tail, similarly to dodecanoyl substitution in lipobactin 1. In some embodiments of the invention such derivatives may include (but not be limited to) Me(OCH$_2$CH$_2$)$_3$CO-$\Delta_{1-5}$-Arg$_{10}$-teixobactin and Me(OCH$_2$CH$_2$)$_4$CO-$\Delta_{1-5}$-Arg$_{10}$-teixobactin.

Example 3: Stereochemistry and Anion Binding Ability of the Peptide Ring

In many embodiments, the relative stereochemistry of macrolactone residues 8-11 is preserved in teixobactin analogues. This depsipeptide ring is one of the most prominent features of teixobactin. As such, it is proposed that understanding the structure-function relations for the residues within and adjacent to the ring will shed light on the origin of the antibacterial properties of teixobactin and help design new potent antimicrobial compounds in accordance with embodiments. To this end, an X-ray crystallographic structure of Ac-$\Delta_{1-5}$-Arg$_{10}$-teixobactin (FIG. 11) as a hydrochloride salt was obtained in accordance with the embodiments of the invention and is shown in FIGS. 12A to 12C.

One notable structural feature observed in the obtained crystal is the relative stereochemistry of the ring's residues affecting the alignment arrangement in which the carbonyl groups of D-Thr$_8$, Ala$_9$, Arg$_{10}$, and Ile$_{11}$ in the peptide point upward, while the amide NH groups of Ala$_9$, Arg$_{10}$, and Ile$_{11}$ point downward (FIG. 12B). In addition, the $\alpha$-amino group of D-Thr$_8$ and the attached residues (Ser$_7$ and Ile$_6$) run downward at almost a right angle to the cyclic depsipeptide ring, as well as the side chain of Arg$_{10}$. Therefore, it appears that all of the ring's NH groups available for hydrogen bonding point in the same direction to allow for enhanced anion binding. Specifically, as seen in FIG. 12B, the amide NH groups of Ile$_{11}$, Ser$_7$, and D-Thr$_8$, as well as the guanidinium group of Arg$_{10}$, form a hydrogen bonding capable cavity equipped to accept and bind a chloride anion. This mode of interaction is similar to that of nisin with the pyrophosphate group of lipid II (S. T. Hsu, E. Breukink, E. Tischenko, M. A. Lutters, B. de Kruijff, R. Kaptein, A. M. Bonvin and N. A. Nuland, Nat. Struct. Mol. Biol., 2004, 11, 963, the disclosures of which are incorporated herein by reference) and, thus, it is expected that the binding cavity of teixobactin and its analogues (315) can also accommodate larger anions, including the pyrophosphate group of lipid II (305) and other related peptidoglycan precursors (FIG. 3). Consequently, in accordance with embodiments, the proper alignment of the functionalities that make-up the anion binding cavity is preserved as it is important for teixobactin and its analogues' ability to bind bacterial cell walls and the overall antimicrobial efficacy.

Figure 13:
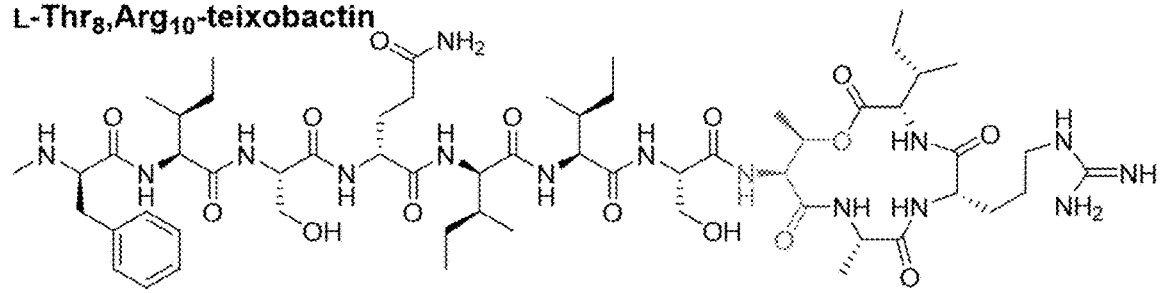
FIG. 13 is a chemical structure drawing of L-$Thr_8$,$Arg_{10}$-teixobactin in accordance with embodiments of the application.
Figure 14:
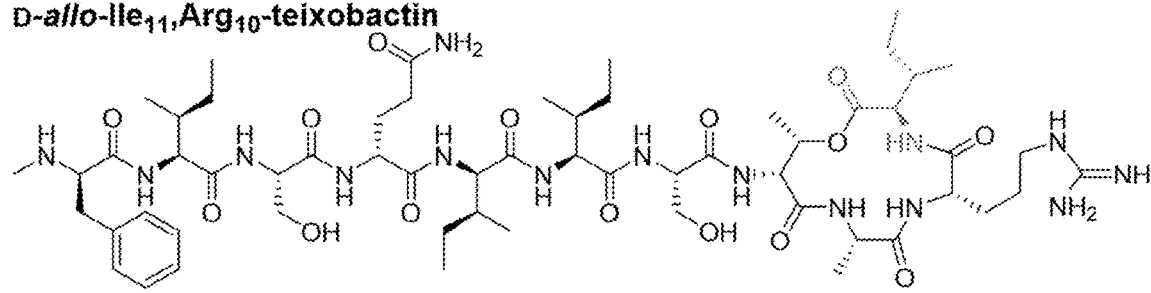
FIG. 14 is a chemical structure drawing of D-allo-$Ile_{11}$, $Arg_{10}$-teixobactin in accordance with embodiments of the application.
Figure 15:
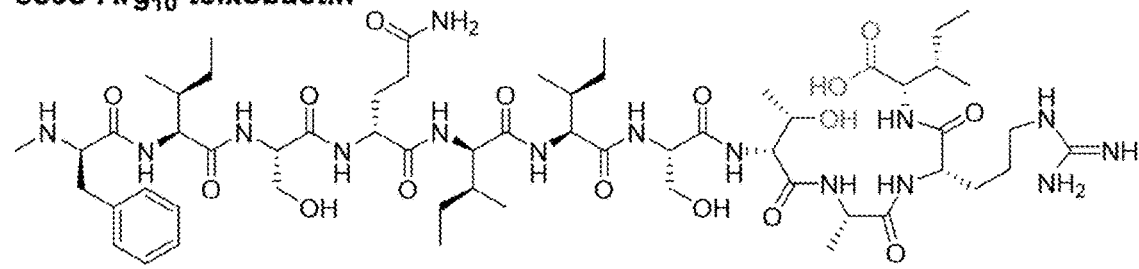
FIG. 15 is a chemical structure drawing of seco-$Arg_{10}$-teixobactin in accordance with embodiments of the application.

Accordingly, in some embodiments, the importance of the macrolactone ring's stereochemistry was further confirmed by the comparison of the antimicrobial activity of various teixobactin's homologues with different depsipeptide stereochemistries. To this end, the diastereomer L-Thr$_8$,Arg$_{10}$-teixobactin (FIG. 13) and D-allo-Ile$_{11}$,Arg$_{10}$-teixobactin (FIG. 14) were prepared according to some embodiments of the invention and compared to Arg$_{10}$-teixobactin. The former proved inactive (MIC>32 µg/mL) against the Gram-positive bacteria, while the latter proved half as active (Table 1). In addition, an acyclic homologue seco-Arg10-teixobactin (FIG. 15) was also prepared according to one embodiment of the invention, and also proved inactive (MIC>32 µg/mL, Table 1), further supporting the importance of the cyclic peptide structure. Collectively, these results suggest that the ring stereochemistry and conformation are important for the antibacterial activity of the teixobactin-based compounds.

Figure 16:
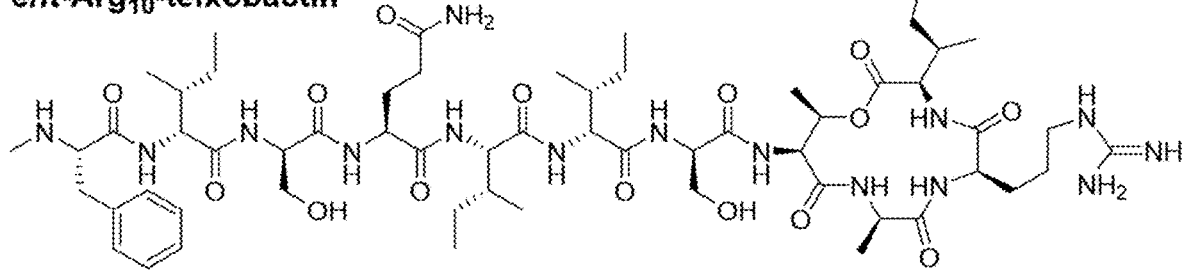
FIG. 16 is a chemical structure drawing of ent-$Arg_{10}$-teixobactin in accordance with embodiments of the application.

Interestingly, ent-Arg$_{10}$-teixobactin analogue (FIG. 16) prepared according to one embodiment, in which the stereochemistry of all of the ring residues is exactly the opposite of the native teixobactin's ring, yet the relative stereochemistry within the ring (i.e. relative alignment of the carbonyl and amide groups) is preserved, exhibits comparable activity to Arg$_{10}$-teixobactin. This exciting finding further supports the nisin-lipid II antibacterial mechanism for teixobactin derivatives.

Figure 12:
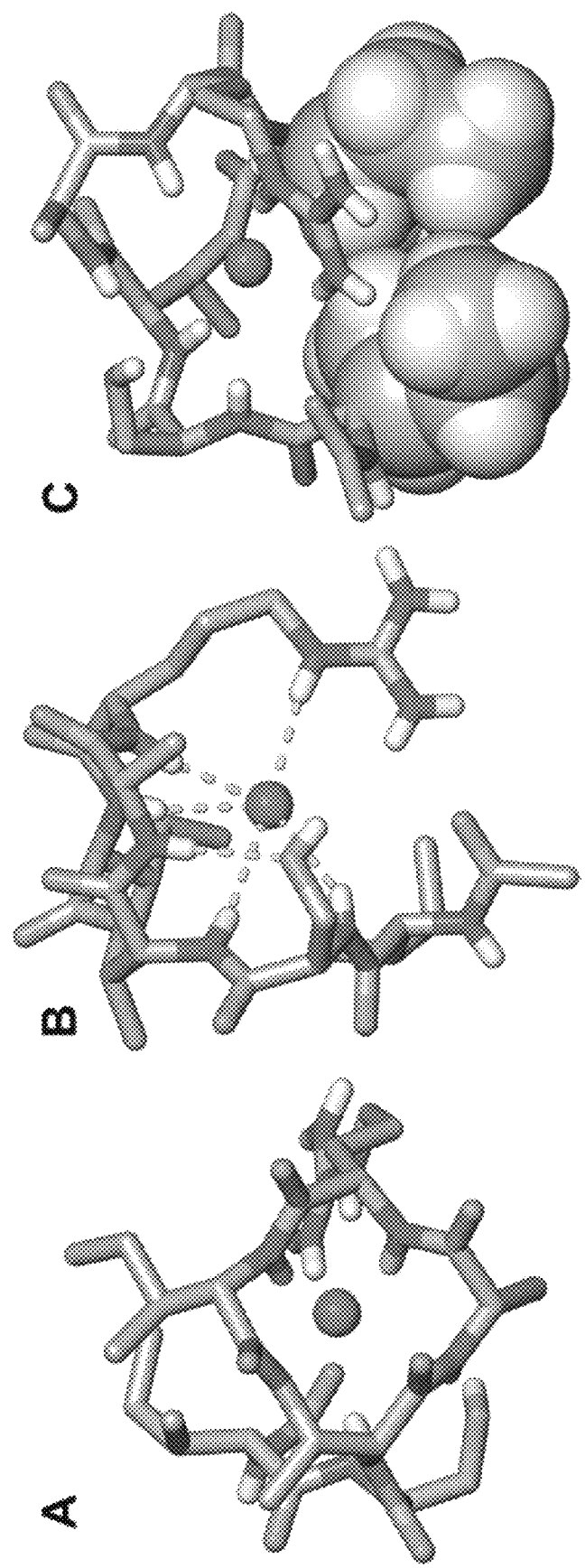
FIGS. 12A to 12C provide the crystal structure of Ac-$\Delta_{1-5}$-$Arg_{10}$-teixobactin in accordance with embodiments of the application.
Figure 17:
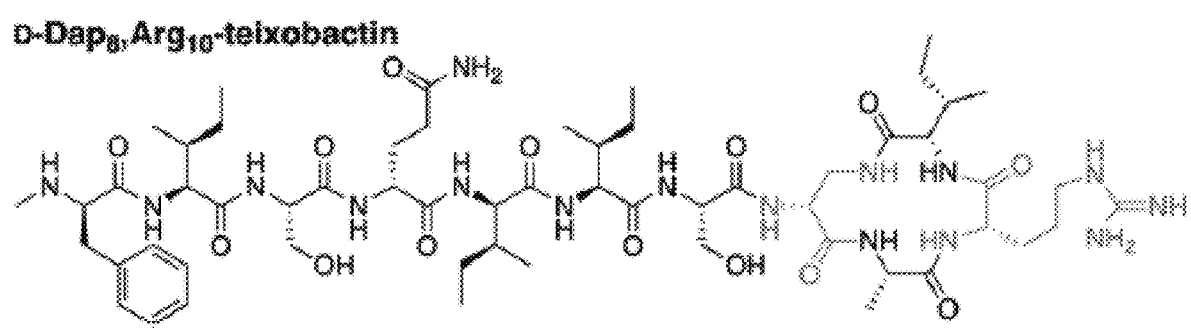
FIG. 17 is a chemical structure drawing of D-$Dap_8$,$Arg_{10}$-teixobactin in accordance with embodiments of the application.

In addition, according to some embodiments stemming from the crystal structure shown in FIG. 12, the hydrogen bonding of the peptide ring to the chloride anion further suggests the possibility of increasing the activity of teixobactin homologues by strengthening the complexation with the pyrophosphate group of lipid II. To explore this idea, D-Thr$_8$ was mutated to D-diaminopropionic acid (D-Dap) to produce D-Dap$_8$,Arg$_{10}$-teixobactin according to some embodiments (FIG. 17). The mutation of D-Thr$_8$ to D-Dap replaces the lactone oxygen atom with a hydrogen bond capable amide NH group; however, this mutation also loses the threonine methyl group. The resulting homologue, shows comparable activity to Arg$_{10}$-teixobactin (Table 2). However, the direct comparison of these two homologues is hampered, because two factors are changed at one time in making this mutation. A reasonable interpretation of this observation is that enhanced activity from replacing the lactone oxygen atom with an H-binding NH group is offset by the increased conformational flexibility of the ring associated with removal of the D-Thr$_8$ methyl group.

In sum, according to many embodiments of the invention, as supported by the X-ray crystal structure studies of a teixobactin homologue, the relative stereochemistry and cyclicity of the teixobactin's depsipeptide is preserved yielding antibacterial properties. In addition, a substitution of the macrolactone's ester with an amide linkage is shown to increase peptide's anion-binding ability and enhance antibacterial properties in various embodiments.

Example 4: Hydrophobicity of Residues H6 and H11

According to many embodiments of the invention, the hydrophobicity of the side chains in residues 6 and 11 is maintained in teixobactin analogues. The importance of this feature for teixobactin's antibacterial activity is supported by both the analysis of the crystal structure shown in FIG. 12 and MIC studies reported in Table 2. Specifically, as seen in FIG. 12A, the side chains of $Ala_9$ and $Ile_{11}$, as well as the methyl group of $D$-$Thr_8$, point outward from the cyclic depsipeptide ring, while the side chains of $Ile_6$ and $Ile_{11}$ are, notably, in loose contact, suggesting a hydrophobic interaction (FIG. 12C). Furthermore, the methyl group of $D$-$Thr_8$ sits near the $Ile_6$ and $Ile_{11}$ side chains, creating a hydrophobic patch.

Figure 18:
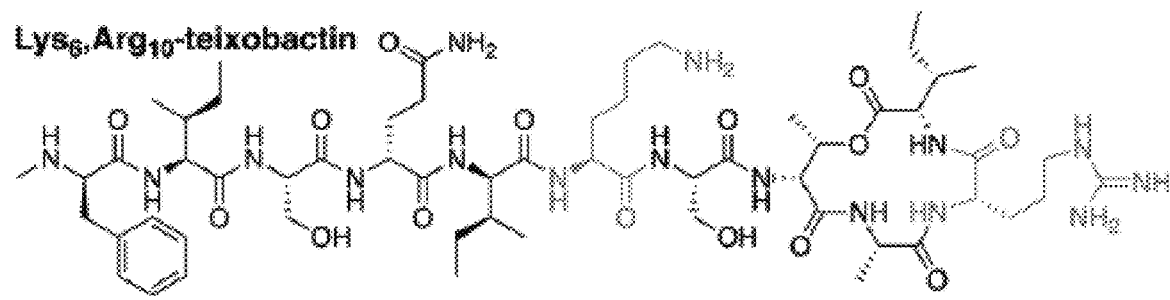
FIG. 18 is a chemical structure drawing of $Lys_6$,$Arg_{10}$-teixobactin in accordance with embodiments of the application.
Figure 19:
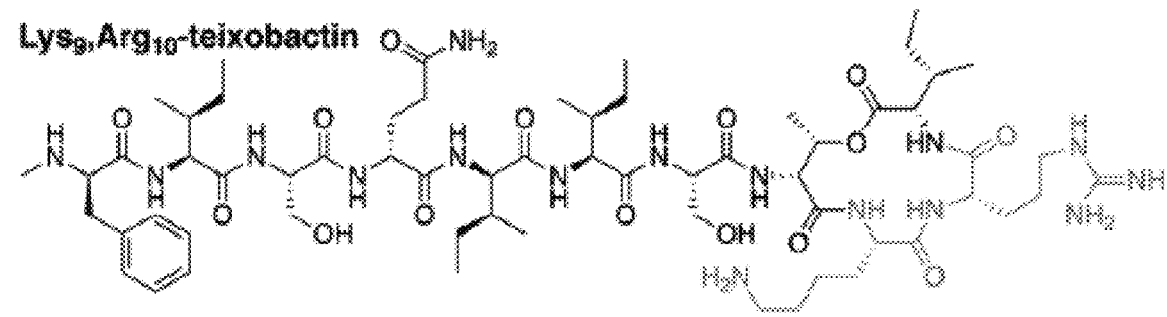
FIG. 19 is a chemical structure drawing of $Lys_6$,$Arg_{10}$-teixobactin in accordance with embodiments of the application.
Figure 20:
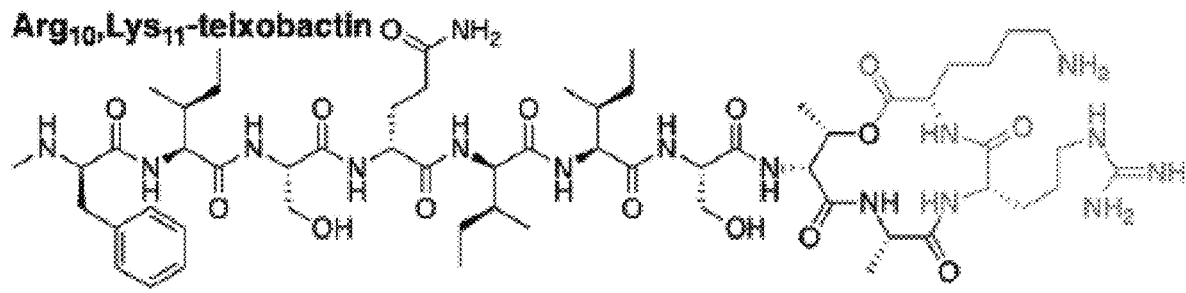
FIG. 20 is a chemical structure drawing of $Arg_{10}$,$Lys_{11}$-teixobactin in accordance with embodiments of the application.

In addition, to explore the roles of the hydrophobic residues at positions 6, 9, and 11, each of these residues were mutated to lysine to produce $Lys_6Arg_{10}$-teixobactin (FIG. 18), $Lys_9Arg_{10}$-teixobactin (FIG. 19), and $Arg_{10}Lys_{11}$-teixobactin (FIG. 20) according to embodiments of the invention, and their antimicrobial activity compared to that of $Arg_{10}$-teixobactin homologue (Table 2). Remarkably, the mutation of either $Ile_6$ or $Ile_{11}$ to lysine results in loss of activity, while mutation of $Ala_9$ to lysine does not (Table 2). This data suggests, according to the embodiments of the invention, that the hydrophobicity of $Ile_6$ and $Ile_{11}$ is important for teixobactin activity, while that of $Ala_9$ is not.

Figure 21:
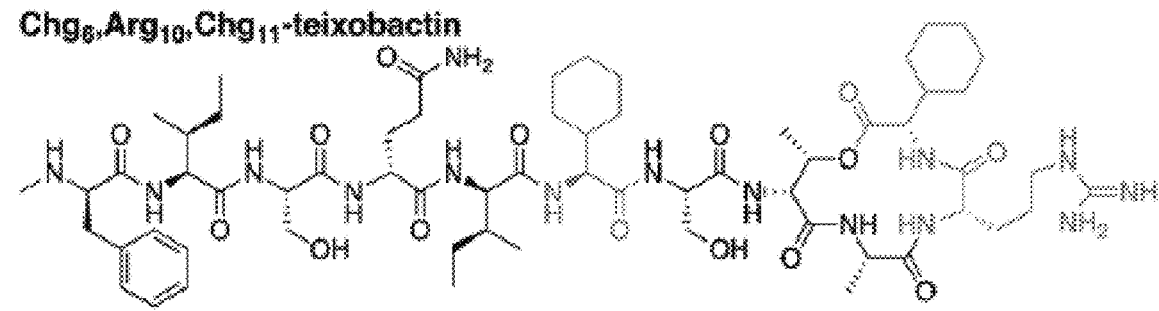
FIG. 21 is a chemical structure drawing of $Chg_6$,$Arg_{10}$, $Chg_{11}$-teixobactin in accordance with embodiments of the application.

To further confirm the role of hydrophobicity at positions 6 and 11 and the contact between the Ile6 and Ile11 side chains, both residues were mutated to cyclohexylglycine (Chg) to produce $Chg_6,Arg_{10},Chg_{11}$-teixobactin (FIG. 21) according to embodiments of the invention. Cyclohexylglycine may be thought of as a homologue of isoleucine, in which two carbons have been added to the sec-butyl side chain to form a cyclohexane ring. The resulting homologue has slightly greater activity than $Arg_{10}$-teixobactin, with three of the four measured MIC values in the Gram-positive bacteria lower by a factor of two (Table 2). This finding further confirms that, according to many embodiments, the hydrophobicity or hydrophobic contact at positions 6 and 11 is important for the antibacterial properties of teixobactin and its analogues.

Example 5: Role of Residue A9

In some embodiments of the invention position 9 of teixobactin's analogues is entirely available for modifications and functionalization as needed to enhance overall compound properties, including (but not limited to) solubility. The availability of position 9 for substitutions and design flexibility was confirmed by both the X-ray crystal structure analysis of teixobactin's analogue and mutation studies according to embodiments.

Figure 22:
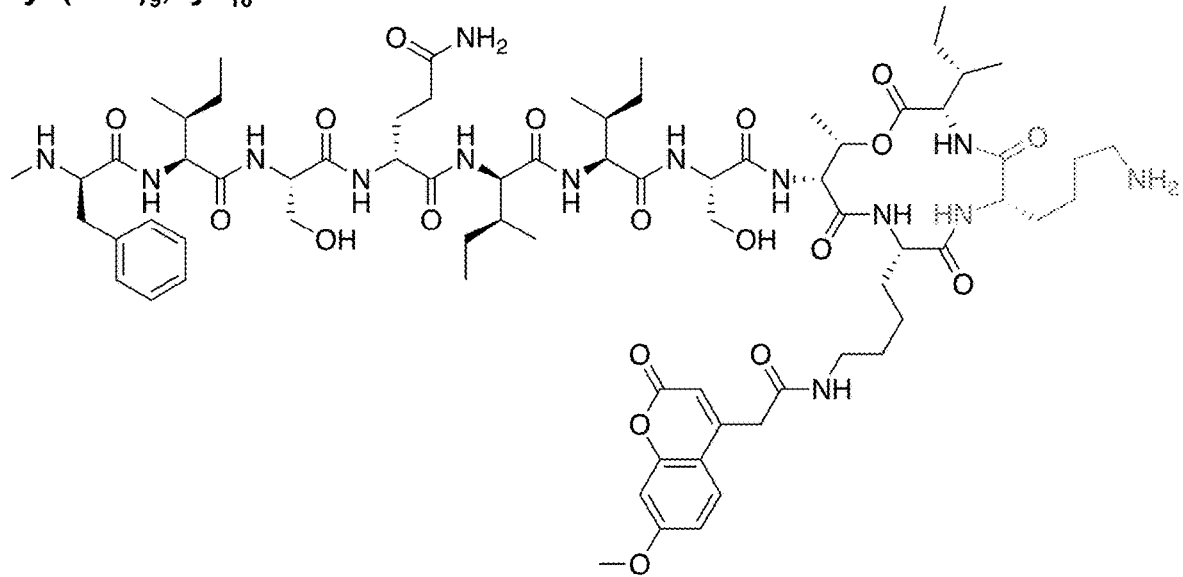
FIG. 22 is a chemical structure drawing of Lys(Mca)$_9$, $Lys_{10}$-teixobactin in accordance with embodiments of the application.
Figure 23:
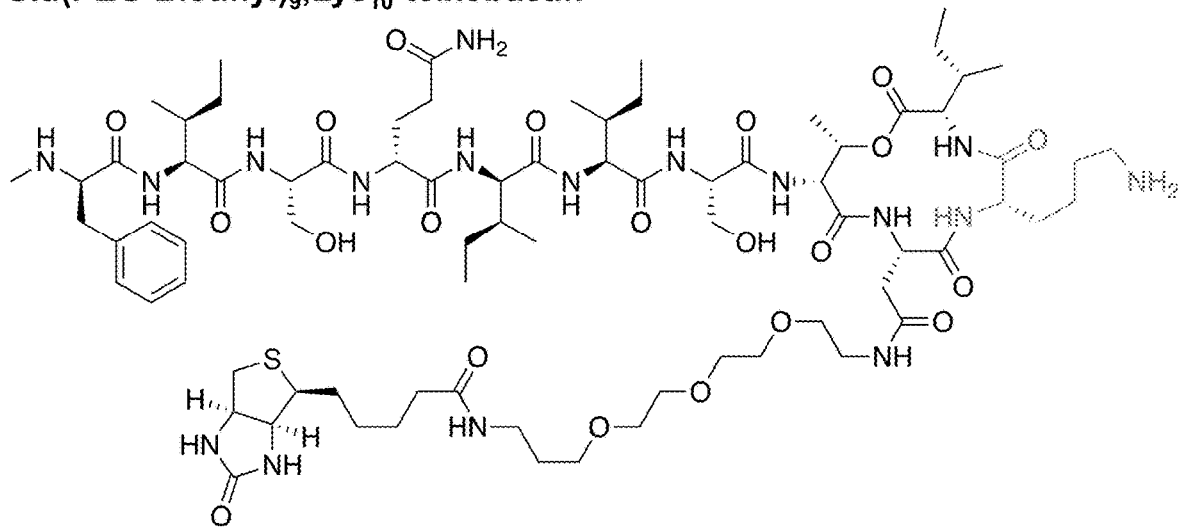
FIG. 23 is a chemical structure drawing of Glu(PEG-Biotinyl)$_9$,$Lys_{10}$-teixobactin in accordance with embodiments of the application.

As such, the outward pointing geometry of the $Ala_9$ side chain (FIG. 12), coupled with the proven activity of $Lys_9$, $Arg_{10}$-teixobactin (Table 2), suggest that position 9 allows functionalization to provide new, completely unnatural, modified homologous of teixobactin that are also active against bacteria. Therefore, a great number of options are potentially available for the design of new or improved teixobactin-based antibiotics, including antibiotics with additional useful features. In some embodiments of the invention, teixobactin-derived compounds can simultaneously serve to both treat and study their interactions with the bacterial infections. For example, analogues of $Lys_{10}$-teixobactin in which $Ala_9$ has been replaced with amino acids bearing coumarin and biotin groups connected by PEG linkers have been prepared according to some embodiments of the invention: $Lys(Mca)_9,Lys_{10}$-teixobactin (FIG. 22) and $Glu(PEG\text{-}Biotinyl)_9,Lys_{10}$-teixobactin (FIG. 23). Both analogues partially retain biological activity with MIC values of 1-8 micrograms/mL and 2-16 micrograms/mL, respectively, for the four species of Gram-positive bacteria (Table 3). As such, these derivatives should be useful as probes for studying the interaction of teixobactin homologues with bacteria by means of fluorescence microscopy and FACS.

In addition, according to many embodiments of the invention, teixobactin homologues can be functionalized at position 9 to improve solubility for easier or more efficient drug administration. For example, $Arg_{10}$-teixobactin has the propensity to form a gel at concentrations as low as 5 mg/mL. This poor solubility will hamper the ability of $Arg_{10}$-teixobactin or any other teixobactin derivative to be used as a drug because it will impede intravenous administration. Therefore, according to some embodiments of the invention, the drug solubility and gelation behavior can be improved via modification of the sites within teixobactin (or its analogue) known to tolerate modifications without loss of activity, such as, for example, described here positions 9 and/or 10. More specifically, in some embodiments of the invention the water solubility of teixobactin analogues can be improved by functionalization of position 9 with polyethylene glycol (PEG) derivatives. In one embodiment, $Ala_9$ is replaced with a PEG-containing amino acid, such as Gln(PEG6OMe), the derivative of Glu, in which the side chain has been coupled to $H_2NCH_2CH_2(OCH_2CH_2)_5OMe$.

Example 6: Serine at Position 7

Figure 24:
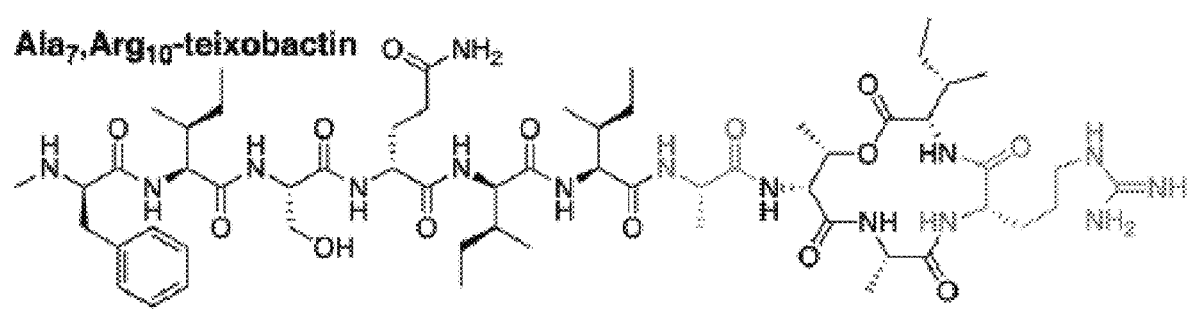

In many embodiments of the invention, serine residue at position 7 is preserved in teixobactin analogues. The importance of hydrogen bond-able serine at position 7 is confirmed by both the X-ray crystal structure analysis and mutation studies. As such, the crystal structure analysis of a teixobactin analogue, first, revealed that the amide group of $Ala_9$ hydrogen bonds to the oxygen atom of the hydroxyl group of $Ser_7$. Next, the importance of preserving the serine residue at position 7 was explored with the help of the serine to alanine mutant $Ala_7,Arg_{10}$-teixobactin (FIG. 24), prepared according to one embodiment of the invention. The resulting homologue showed greatly diminished activity (Table 2), confirming the importance of serine residue at position 7 for the antibacterial properties of teixobactin and its analogues according to embodiments of the invention.

In addition, in some embodiments of the invention, the solubility of teixobactin analogues can be enhanced via a prodrug strategy involving $Ser_7$. According to such embodiments, prior to administration of the treatment, $Ser_7$ (and/or $Ser_3$) are esterified with solubility-enhancing amino acids or dipeptides. In some such embodiments, the resulting Ser-O-AA-$NH^{3+}$ or Ser-O-AA-AA-$NH^{3+}$ derivatives (where AA is an amino acid residue) will have enhanced solubility and, once in the bloodstream, will convert to the parent teixobactin derivative without forming a gel.

Example 7: Synthesis of $Arg_{10}$-Teixobactin and Other Homologues

Figure 25:
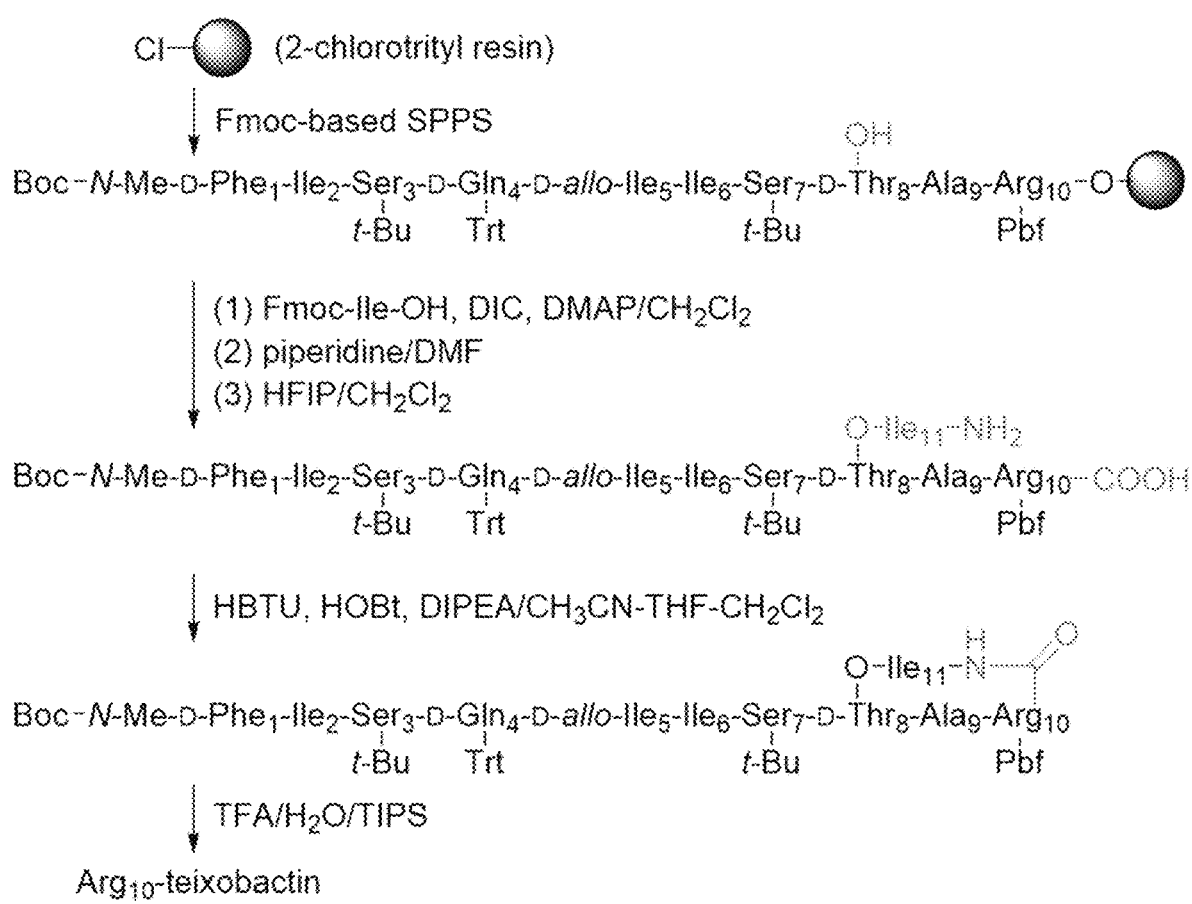
FIG. 25 is flow chart schematic of $Arg_{10}$-teixobactin synthesis, in accordance with embodiments of the application.

In many embodiments, $Arg_{10}$-teixobactin and other homologues were synthesized by SPPS on 2-chlorotrityl chloride resin, followed by solution-phase macrolactamization to form the $Arg_{10}$-$Ile_{11}$ amide bond (FIG. 25). Fmoc protecting groups were used to construct all of the amide bonds and carried $D$-$Thr_8$ through the entire synthesis without side chain protection. All homologues were prepared and studied as the trifluoroacetic acid (TFA) salts.

The synthesis began by attaching Fmoc-Arg(Pbf)-OH to 2-chlorotrityl chloride resin. Residues 9 through 1 were then introduced by standard Fmoc-based SPPS using HCTU as the coupling reagent. $D$-$Thr_8$ was introduced without a protecting group at the hydroxy position. No O-acylation of D-Thr$_8$ was observed in the subsequent rounds of SPPS. D-Thr$_8$ was then O-acylated with Fmoc-Ile-OH using DIC and DMAP. Fmoc-deprotection, followed by cleavage from the resin with 20% hexafluoroisopropanol (HFIP) in CH$_2$Cl$_2$ afforded the linear precursor. Macrolactamization with HBTU and HOBt, followed by global deprotection with trifluoroacetic acid (TFA) and RP-HPLC purification afforded Arg$_{10}$-teixobactin. A series of homologues were also prepared using similar procedures. The details of the Arg$_{10}$-teixobactin synthesis are described in the subsequent paragraphs.

Resin Loading.

2-Chlorotrityl chloride resin (300 mg, 1.2 mmol/g) was added to a 10 mL Bio-Rad Poly-Prep chromatography column. The resin was suspended in dry CH$_2$Cl$_2$ (10 mL) and allowed to swell for 30 min. The resin was loaded with a solution of Fmoc-Arg(Pbf)-OH (117 mg, 0.18 mmol, 0.50 equiv) and 2,4,6-collidine (300 µL) in dry CH$_2$Cl$_2$ (5 mL). The suspension was agitated for 12 h. The solution was drained, and the resin was washed with dry CH$_2$Cl$_2$ (3×). A mixture of CH$_2$Cl$_2$/MeOH/DIPEA (17:2:1, 8 mL) was added to the resin and agitated for 1 h to cap any unreacted resin sites. The solution was drained, and the resin was washed with dry CH$_2$Cl$_2$ (3×). The resin loading was determined to be 0.09 mmol [0.29 mmol/g, 48% loading] through UV analysis of the Fmoc cleavage product.

Peptide Coupling.

The loaded resin was suspended in dry DMF and transferred to a solid-phase peptide synthesis reaction vessel for automated peptide coupling with Fmoc-protected amino acid building blocks. The linear peptide was synthesized through the following cycles: i. Fmoc deprotection with 20% (v/v) piperidine in dry DMF (3 mL) for 10 min, ii. resin washing with dry DMF (3×), iii. coupling of amino acid (0.36 mmol, 4 equiv) with HCTU (142 mg, 0.36 mmol, 4 equiv) in 20% (v/v) 2,4,6-collidine in dry DMF (3 mL) for 20 min, and iv. resin washing with dry DMF (6×). For D-to-L and L-to-D amino acid couplings, the reaction time in step iii was increased to 1 h. After completing the linear synthesis, the resin was transferred to a 10 mL Bio-Rad Poly-Prep chromatography column. The resin was then washed with dry DMF (3×) and dry CH$_2$Cl$_2$ (3×).

Esterification.

In a test tube, Fmoc-Ile-OH (303 mg, 0.90 mmol, 10 equiv) and diisopropylcarbodiimide (140 µL, 0.90 mmol, 10 equiv) were dissolved in dry CH$_2$Cl$_2$ (5 mL). The resulting solution was filtered through 0.20 µm nylon filter, and then 4-dimethylaminopyridine (11 mg, 0.09 mmol, 1 equiv) was added to the filtrate. The resulting solution was transferred to the resin and was gently agitated for 1 h. The solution was drained and the resin was washed with dry CH$_2$Cl$_2$ (3×) and DMF (3×).

Fmoc Deprotection and Cleavage of the Linear from the Resin.

The Fmoc protecting group on Ile11 was removed by adding 20% piperidine in dry DMF (5 mL) for 30 min. The solution was drained, and the resin was washed with dry DMF (3×) and then with dry CH$_2$Cl$_2$ (3×). To cleave the peptide, the resin was treated with 20% hexafluoroisopropanol in dry CH$_2$Cl$_2$ (6 mL) followed by gentle agitation for 1 h. The filtrate was collected in a round-bottomed flask. The resin was washed with a second aliquot of 20% hexafluoroisopropanol (6 mL) and then washed with dry CH$_2$Cl$_2$ (3×). The filtrates were combined and concentrated under reduced pressure to afford a clear oil. The oil was placed under vacuum (<10 mTorr) to remove any residual solvents.

Cyclization.

The oil was dissolved in a mixture of CH$_3$CN/THF/CH$_2$Cl$_2$ (6:2:2, 10 mL). HBTU (195 mg, 0.54 mmol, 6 equiv) and HOBt (70 mg, 0.54 mmol, 6 equiv) were added to solution. The reaction mixture was stirred under nitrogen for 30 min. DIPEA (94 µL, 0.54 mmol, 6 equiv) was slowly added to the solution and the reaction mixture was stirred for 2 h. The mixture was concentrated under reduced pressure to afford the cyclized peptide as a white solid. The solid was placed under vacuum (<10 mTorr) to remove any residual solvents.

Global Deprotection and Purification of Arg$_{10}$-Teixobactin.

The crude protected peptide was dissolved in a mixture of trifluoroacetic acid (TFA)/triisopropylsilane/H$_2$O (90:5:5, 10 mL) and stirred under nitrogen for 1 h. The resulting solution was then concentrated under reduced pressure to afford the deprotected peptide as a clear yellow oil. The oil was dissolved in 20% (v/v) CH$_3$CN in water (5 mL) and centrifuged at 14,000 rpm for 5 min, and the solution was filtered through 0.20 µm nylon filter. The peptide was purified by reverse-phase HPLC with H$_2$O/CH$_3$CN (gradient elution of 20-50% CH$_3$CN w/0.1% TFA). Pure fractions analyzed by analytical HPLC and electrospray ionization (ESI) mass spectrometry were combined and lyophilized. Arg$_{10}$-teixobactin was isolated as the trifluoroacetic acid (TFA) salt of a 14.2 mg white powder (11.6% yield based on resin loading).

Esterification with DIC and DMAP is known to epimerize amino acids. 1H NMR analysis of the unpurified Arg$_{10}$-teixobactin, and comparison to an authentic sample of D-allo-Ile$_{11}$,Arg$_{10}$-teixobactin, showed approximately 33% epimerization. HPLC purification of the crude product afforded Arg$_{10}$-teixobactin in approximately 95% diastereomeric purity.

The other teixobactin homologues were prepared using similar procedures. All teixobactin homologues were estimated to be at least 90% purity based on RP-HPLC and 1H NMR analysis, with the exception of ent-Arg$_{10}$-teixobactin, which showed a 16 mol % impurity in the 1H NMR spectrum. This impurity is suspected to arise from a stereoisomeric impurity at the L-allo-Ile5 position, which could result from stereoisomeric impurity in the Fmoc-L-allo-Ile-OH that was used in the synthesis.

Yields of the various teixobactin homologues, in accordance with embodiments, are provided in Table 4, below.

TABLE 4

YIELD OF TEIXOBACTIN HOMOLOGUES

| Homologue | yield (mg) | % yield | calcd. MW as TFA salt |
|---|---|---|---|
| Arg$_{10}$-teixobactin | 14.2 mg | 10.7% | 1472.54 (•2 TFA) |
| Lys$_{10}$-teixobactin | 14.2 mg | 10.9% | 1444.53 (•2 TFA) |
| L-Thr$_8$,Arg$_{10}$-teixobactin | 4.7 mg | 3.6% | 1472.54 (•2 TFA) |
| D-allo-Ile$_{11}$,Arg$_{10}$-teixobactin | 13.2 mg | 10.0% | 1472.54 (•2 TFA) |
| seco-Arg$_{10}$-teixobactin | 13.2 mg | 9.8% | 1490.56 (•2 TFA) |
| ent-Arg$_{10}$-teixobactin | 11.5 mg | 8.7% | 1472.54 (•2 TFA) |
| short-Arg$_{10}$-teixobactin | 9.7 mg | 12.4% | 869.81 (•2 TFA) |
| lipobactin 1 | 12.1 mg | 14.1% | 956.10 (•1 TFA) |

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:
1. Antimicrobial compound comprising
a teixobactin homologue as set forth by:

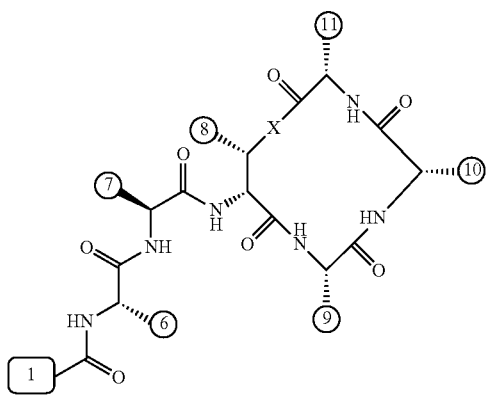

wherein position 10 is comprised of lysine;
wherein position 1 is comprised of at least one of the following species selected from the group consisting of:
N-Me-D-Phe$_1$-Ile$_2$-Ser$_3$-D-Gln$_4$-D-allo-Ile$_5$, and an acyl group having a hydrophobic chain;
wherein the linkage X between positions 8 and 11 is an ester;
wherein positions 6 and 11 are each comprised of isoleucine;
wherein position 8 is comprised of threonine;
wherein position 9 is comprised of alanine; and
wherein position 7 is comprised of serine.
2. The antimicrobial compound of claim 1, wherein the teixobactin homologue is Lys$_{10}$-teixobactin.
3. The antimicrobial compound of claim 1, wherein position 1 comprises a dodecanoyl group.
4. A biological probe comprising:
a teixobactin homologue as set forth by:

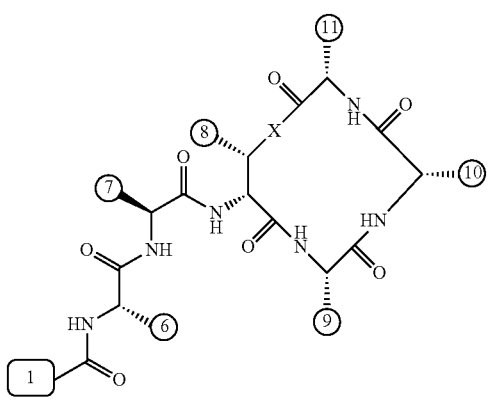

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;
wherein position 1 is comprised of at least one of the following species selected from the group consisting of a sequence of at least one natural or unnatural amino acid comprising at least one hydrophobic side chain, and an acyl group having a hydrocarbon chain;
wherein the linkage X between positions 8 and 11 is one of either an ester or an amide;
wherein positions 6 and 11 are comprised of either the same or different natural or unnatural amino acids, said amino acids each having a hydrophobic side chain;
wherein position 8 is comprised of threonine or D-diaminopropionic acid;
wherein position 9 is comprised of any natural or unnatural amino acid having a biological marker or probe attached thereto; and
wherein position 7 is comprised of serine or another natural or unnatural amino acid having a side chain hydroxyl group.
5. A prodrug comprising:
a teixobactin homologue as set forth by:

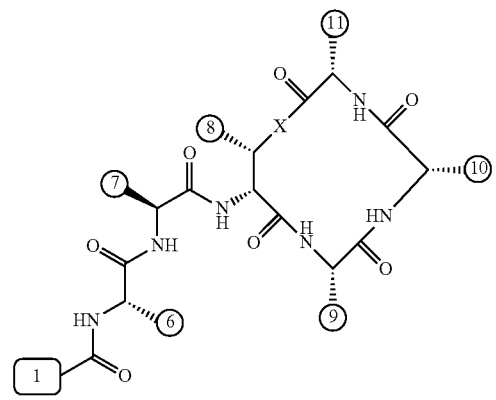

wherein position 10 is comprised of a natural or unnatural amino acid comprising a functionality selected from the group consisting of: guanidinium, imidazoles, amines, alcohols, other hydrogen bonding-capable groups, hydrogen, hydrophilic or hydrophobic groups, and any derivatives or analogues thereof;
wherein position 1 is comprised of at least one of the following species selected from the group consisting of a sequence of at least one natural or unnatural amino acid comprising at least one hydrophobic side chain, and an acyl group having a hydrocarbon chain;
wherein the linkage X between positions 8 and 11 is one of either an ester or an amide;
wherein positions 6 and 11 are comprised of either the same or different natural or unnatural amino acids, said amino acids each having a hydrophobic side chain;
wherein position 8 is comprised of threonine or D-diaminopropionic acid;
wherein position 9 is comprised of any natural or unnatural amino acid; and
wherein position 7 is comprised of an esterified serine or another natural or unnatural amino acid having a side chain hydroxyl group, wherein the esterified serine or other natural or unnatural amino acid has a solubilizing functionality attached thereto.

6. A method of treating a microbial infection comprising:

administering a therapeutically effective amount of a teixobactin homologue to a patient having a microbial infection;

wherein the teixobactin homologue is set forth by:

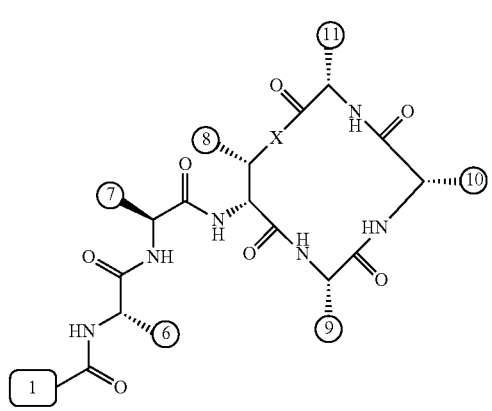

wherein position 10 is comprised of lysine;
wherein position 1 is comprised of at least one of the following species selected from the group consisting of:
N-Me-D-Phe$_1$-Ile$_2$-Ser$_3$-D-Gln$_4$-D-allo-Ile$_5$, and
an acyl group having a hydrophobic chain;
wherein the linkage X between positions 8 and 11 is an ester;
wherein positions 6 and 11 are each comprised of isoleucine;
wherein position 8 is comprised of threonine;
wherein position 9 is comprised of alanine; and
wherein position 7 is comprised of serine.

7. An antimicrobial medicinal composition comprising:
a vehicle or excipient; and
a therapeutically effective amount of a teixobactin homologue set forth by:

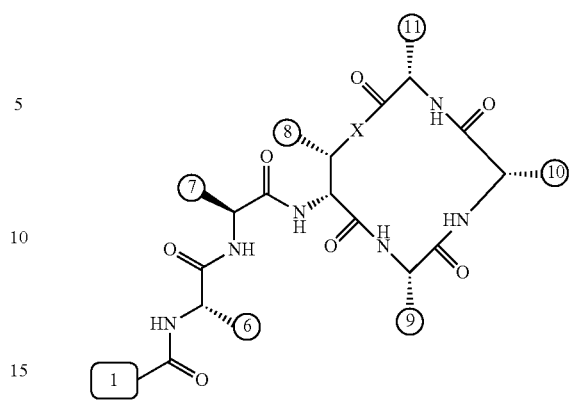

wherein position 10 is comprised of lysine;
wherein position 1 is comprised of at least one of the following species selected from the group consisting of:
N-Me-D-Phe$_1$-Ile$_2$-Ser$_3$-D-Gln$_4$-D-allo-Ile$_5$, and
an acyl group having a hydrophobic chain;
wherein the linkage X between positions 8 and 11 is an ester;
wherein positions 6 and 11 are each comprised of isoleucine;
wherein position 8 is comprised of threonine;
wherein position 9 is comprised of alanine; and
wherein position 7 is comprised of serine.

8. The antimicrobial medicinal compound composition of claim 7, wherein the teixobactin homologue comprises Lys$_{10}$-teixobactin.

9. The antimicrobial compound of claim 1, wherein position 1 comprises an acyl group having a C$_{6-20}$ alkyl chain.

10. The antimicrobial compound of claim 1, wherein position 1 comprises an acyl group having a C$_{11}$ alkyl chain.

11. The antimicrobial medicinal composition of claim 7, wherein position 1 comprises a dodecanoyl group.

12. The antimicrobial medicinal composition of claim 7, wherein position 1 comprises an acyl group having a C$_{6-20}$ alkyl chain.

13. The antimicrobial medicinal composition of claim 7, wherein position 1 comprises an acyl group having a C$_{11}$ alkyl chain.

14. The method of claim 6, wherein the teixobactin homologue comprises Lys$_{10}$-teixobactin.

15. The method of claim 6, wherein position 1 comprises a dodecanoyl group.

16. The method of claim 6, wherein position 1 comprises an acyl group having a C$_{6-20}$ alkyl chain.

17. The method of claim 6, wherein position 1 comprises an acyl group having a C$_{11}$ alkyl chain.

* * * * *